(12) United States Patent
Artemiadis et al.

(10) Patent No.: US 9,833,895 B2
(45) Date of Patent: Dec. 5, 2017

(54) COUPLING SYSTEM

(71) Applicant: Arizona Board of Regents on Behalf of Arizona State University, Tempe, AZ (US)

(72) Inventors: Panagiotis Artemiadis, Phoenix, AZ (US); Gerald O'Neill, Tempe, AZ (US)

(73) Assignee: Arizona Board of Regents on behalf of Arizona State University, Tempe, AZ (US)

(*) Notice: Subject to any disclaimer, the term of this patent is extended or adjusted under 35 U.S.C. 154(b) by 196 days.

(21) Appl. No.: 14/438,958

(22) PCT Filed: Oct. 28, 2013

(86) PCT No.: PCT/US2013/067114
§ 371 (c)(1),
(2) Date: Apr. 28, 2015

(87) PCT Pub. No.: WO2014/070672
PCT Pub. Date: May 8, 2014

(65) Prior Publication Data
US 2015/0336263 A1    Nov. 26, 2015

Related U.S. Application Data

(60) Provisional application No. 61/719,794, filed on Oct. 29, 2012.

(51) Int. Cl.
*A61H 1/02* (2006.01)
*B25J 9/00* (2006.01)
(Continued)

(52) U.S. Cl.
CPC .............. *B25J 3/00* (2013.01); *A61F 5/01* (2013.01); *B25J 9/0081* (2013.01); *B25J 11/00* (2013.01); *B25J 17/00* (2013.01); *G05B 2219/40305* (2013.01); *Y10T 29/49828* (2015.01); *Y10T 403/32114* (2015.01)

(58) Field of Classification Search
None
See application file for complete search history.

(56) References Cited

U.S. PATENT DOCUMENTS 6,069,415 A * 5/2000 Little ..................... F16P 7/00
307/326
6,301,526 B1   10/2001 Kim et al.
(Continued)

FOREIGN PATENT DOCUMENTS

KR   10-2009-0098340 A   9/2009
KR   10-2011-0120565 A   4/2011

OTHER PUBLICATIONS

International Search Report from International Patent Application Publication No. WO 2014/070672, dated Jan. 28, 2014, pp. 1-2.

*Primary Examiner* — Joshua J Michener
*Assistant Examiner* — Kyle Walraed-Sullivan
(74) *Attorney, Agent, or Firm* — Polsinelli PC; Ari M. Bai

(57) ABSTRACT

Embodiments of a coupling system include a brace member, a plurality of coupling members, and a plurality of magnetic bodies that permit an individual to be attached or detached from a robotic device. The coupling system may serve as a detachable interface between an individual engaged to the robotic device.

30 Claims, 20 Drawing Sheets

(51) Int. Cl.
*A61F 5/01* (2006.01)
*B25J 3/00* (2006.01)
*B25J 11/00* (2006.01)
*B25J 17/00* (2006.01)

(56) References Cited

U.S. PATENT DOCUMENTS

| | | | | |
|---|---|---|---|---|
| 6,690,208 | B2* | 2/2004 | Gloden | B25J 19/063 |
| | | | | 192/150 |
| 8,221,248 | B2* | 7/2012 | Wang | B25J 19/063 |
| | | | | 464/162 |
| 8,235,827 | B2 | 8/2012 | Shim et al. | |
| 8,794,418 | B1* | 8/2014 | Norton | B25J 17/0208 |
| | | | | 192/150 |
| 9,381,642 | B2* | 7/2016 | Asada | B25J 5/00 |
| 2003/0223844 | A1* | 12/2003 | Schiele | A61H 1/0274 |
| | | | | 414/5 |
| 2004/0106881 | A1* | 6/2004 | McBean | A61B 5/04888 |
| | | | | 601/5 |
| 2004/0128850 | A1* | 7/2004 | Joo | B25J 17/0208 |
| | | | | 33/644 |
| 2007/0032884 | A1* | 2/2007 | Veatch | A61F 2/54 |
| | | | | 623/64 |
| 2007/0225620 | A1* | 9/2007 | Carignan | A61H 1/0281 |
| | | | | 601/5 |
| 2009/0221943 | A1* | 9/2009 | Burbank | A61H 1/008 |
| | | | | 601/46 |
| 2009/0233720 | A1* | 9/2009 | Shim | B25J 17/0208 |
| | | | | 464/38 |
| 2010/0144501 | A1* | 6/2010 | Berhanu | A63B 21/072 |
| | | | | 482/139 |
| 2010/0160844 | A1* | 6/2010 | Gilbert | A61F 2/64 |
| | | | | 602/16 |
| 2010/0204804 | A1* | 8/2010 | Garrec | A61H 1/0277 |
| | | | | 623/24 |
| 2010/0278623 | A1* | 11/2010 | Blank | B25J 9/101 |
| | | | | 414/749.1 |
| 2011/0251533 | A1 | 10/2011 | Han et al. | |
| 2011/0301718 | A1* | 12/2011 | Carter | A63B 71/0009 |
| | | | | 623/57 |
| 2012/0101419 | A1* | 4/2012 | Bonutti | A61F 5/013 |
| | | | | 602/20 |
| 2012/0264576 | A1* | 10/2012 | Goeckel | A63B 21/0004 |
| | | | | 482/124 |
| 2013/0333368 | A1* | 12/2013 | Durfee | F01B 11/04 |
| | | | | 60/370 |
| 2014/0039644 | A1* | 2/2014 | Dillingham | A61F 2/60 |
| | | | | 623/36 |
| 2014/0094351 | A1* | 4/2014 | Cersonsky | A63B 21/0004 |
| | | | | 482/115 |
| 2015/0018738 | A1* | 1/2015 | Fried | A61F 5/013 |
| | | | | 602/21 |
| 2015/0150704 | A1* | 6/2015 | Hu | A61F 5/0102 |
| | | | | 602/16 |
| 2015/0173992 | A1* | 6/2015 | Wang | A61H 1/02 |
| | | | | 601/5 |
| 2015/0272807 | A1* | 10/2015 | Gupta | A61H 1/0274 |
| | | | | 601/33 |

* cited by examiner

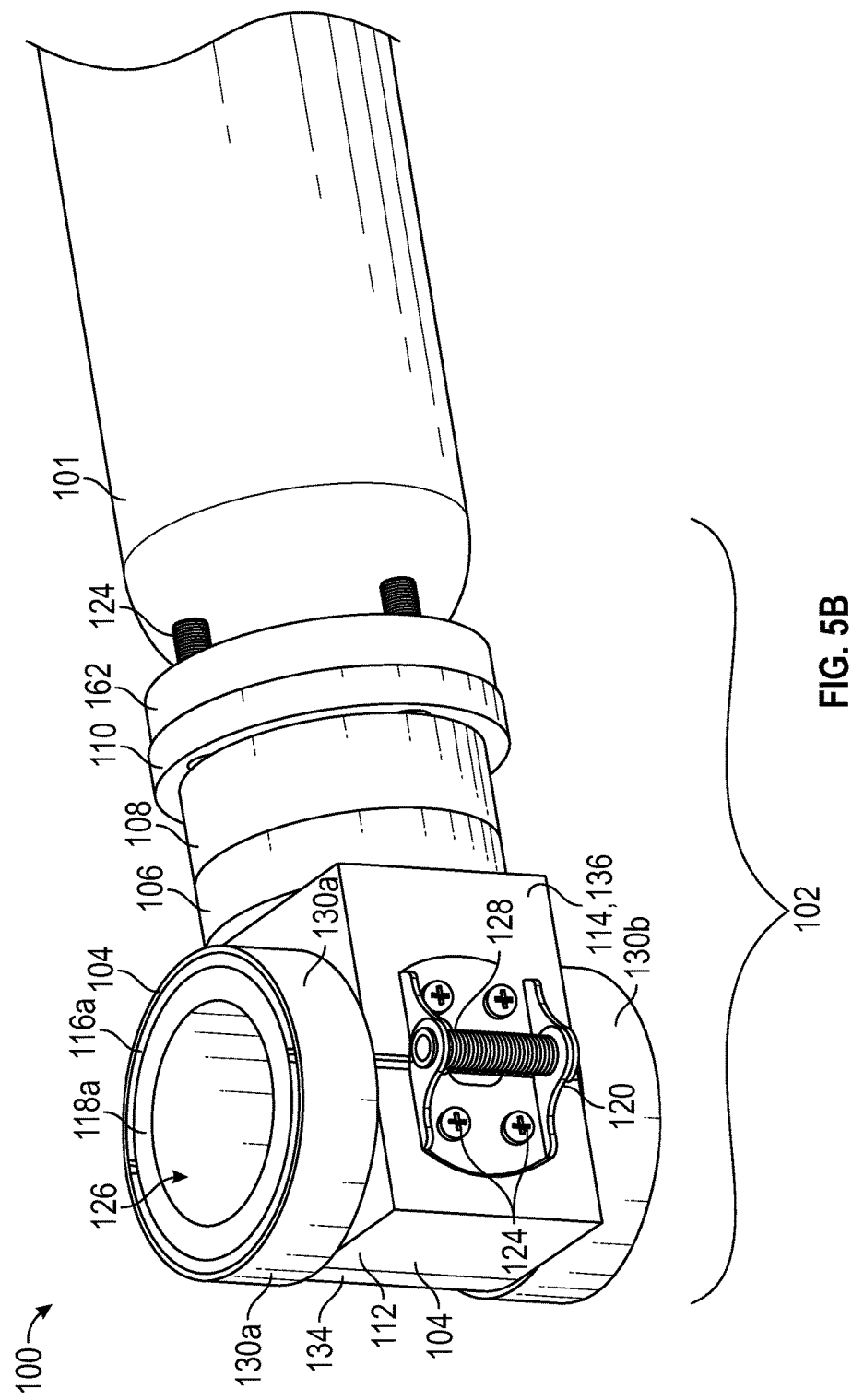

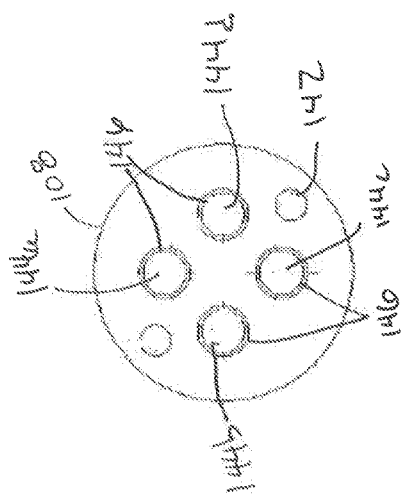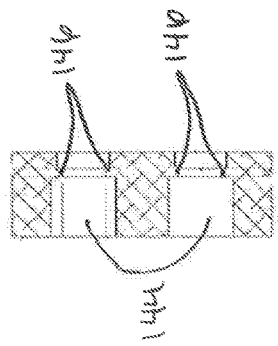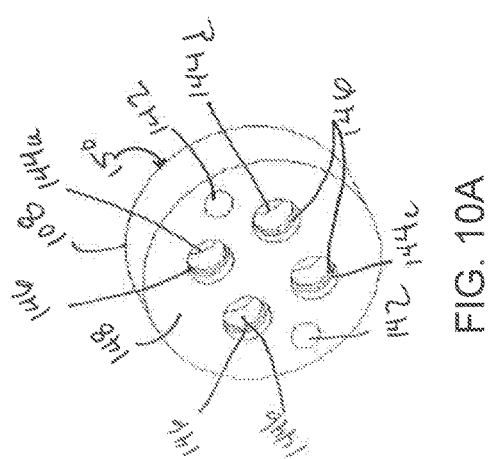

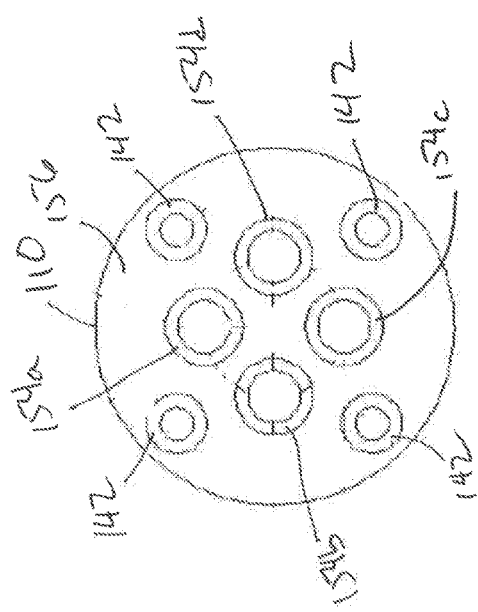
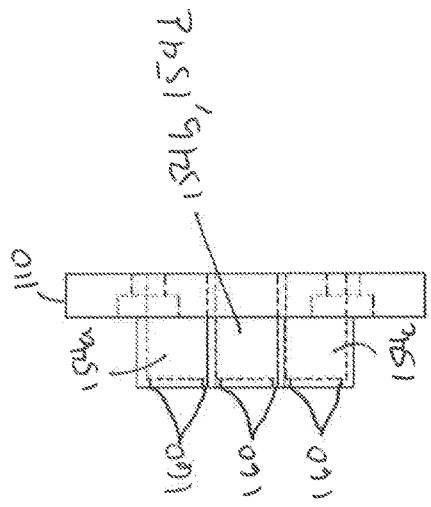
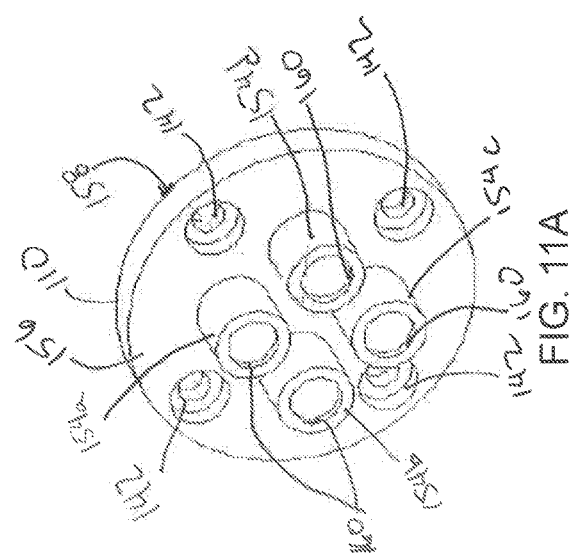

COUPLING SYSTEM

CROSS-REFERENCE TO RELATED APPLICATIONS

The present application claims priority to POT Application No. PCT/US2013/067114 filed on Oct. 28, 2013, which claims priority to U.S. Provisional Application No. 61/719,794 filed on Oct. 29, 2012, the entire contents and disclosure of which are herein incorporated by reference.

FIELD

This disclosure is related generally to the field of human-machine interfaces and in particular to a system and method for coupling together a portion of a human (e.g., a limb) with a robotic device.

BACKGROUND

In general, robotic exoskeletons or other robotic limbs can be used in multiple capacities, such as military, industrial, augmentative, rehabilitative, or for research-related applications. For example, individuals who have suffered an injury or disease (e.g., a stroke) and require retraining or rehabilitation of one or more limbs and motor skills may employ a robotic exoskeleton to assist in their rehabilitation. Moreover, some robotic exoskeletons or other robotic devices can be used in military applications to augment strength and speed for use in combat and other military-related activities. In addition, some robotic devices can be used in industrial settings for use in shipping, loading, and other applications to accomplish movement of relatively large masses and/or volumes in a relatively short period of time.

Regardless of the uses of these robotic devices, many of these conventional systems require that the human be physically coupled to the robotic device. By coupling together the human and the robotic device, the human can be put at risk. In particular, because many of these couplings do not readily uncouple, if the robotic device were to not perform in accordance with a pre-programmed protocol, the human could face significant injury. As such, many of these conventional systems may use coupling devices such as screws, bolts, or straps to retain the interface between the human and the robotic device. As a result, it may be difficult to separate the coupling between the human and the robotic device should a need arise for these two entities to be quickly separated, for example, during an emergency. Therefore, there is a need for further improvements in coupling systems that couple a human limb to a robotic device.

SUMMARY

In one embodiment, a coupling system can include a brace member, a plurality of coupling members, and a plurality of magnetic bodies. For example, in one embodiment, the coupling system can be coupled or affixed to a robotic device to serve as an interface therebetween. In one embodiment, the brace member can include a first portion pivotally coupled to a second portion. Once coupled, the first and second portion can collectively define a sleeve channel. The plurality of coupling members can include a first coupling member that can be engaged to the brace member and another of the coupling member that can define a plurality of pegs. In addition, in some embodiments, a third of the plurality of coupling members defines a plurality of corresponding channels configured to receive a respective one of the plurality of pegs. In one embodiment, at least one of the plurality of magnetic bodies can be disposed within any two of the plurality of pegs and at least another one of the plurality of magnetic bodies can be disposed with any two of the plurality of channels.

Some embodiments provide a method of assembling a coupling system. For example, the method may include coupling a first portion to a second portion to form a brace member such that the brace member defines at least a portion of a sleeve channel. The method may also include coupling a proximal coupling member to the brace member and coupling a medial coupling member to the proximal coupling member. In some aspects, the medial coupling member may include a plurality of channels. The method may further include coupling a distal coupling member to a robotic device. In particular, the distal coupling member may include a plurality of pegs that can be configured and arranged to be received within plurality of channels of the medial coupling member. In some aspects, the method includes providing a plurality of magnetic bodies, with at least a portion of the plurality of magnetic bodies being disposed within any two of the plurality of the pegs and any two of the plurality of channels.

In one embodiment, a coupling apparatus can include a brace member, a plurality of coupling members, and a plurality of magnetic bodies. For example, in one embodiment, plurality of coupling members can include a proximal, medial, and a distal coupling member, with the proximal coupling member capable of being coupled to the brace member and the medial coupling member capable of being coupled to the proximal coupling member. In one embodiment, the brace member can include a first portion pivotally coupled to a second portion. Once coupled, the first and second portion can collectively define a sleeve channel. The distal coupling member can define a plurality of pegs. In addition, in some embodiments, the medial coupling member can define a plurality of corresponding channels configured to receive a respective one of the plurality of pegs. In one embodiment, at least one of the plurality of magnetic bodies can be disposed within any two of the plurality of pegs and at least another one of the plurality of magnetic bodies can be disposed with any two of the plurality of channels.

Additional objectives, advantages and novel features will be set forth in the description which follows or will become apparent to those skilled in the art upon examination of the drawings and detailed description which follows.

BRIEF DESCRIPTION OF THE DRAWINGS

FIG. 5B is a second perspective view of the coupling system of FIG. 5A;

FIG. 10A is a perspective view of one embodiment of a medial coupling member for the coupling system;

FIG. 10B is a front view of the medial coupling member of FIG. 10A;

FIG. 10C is a cross-sectional view of the medial coupling member of FIG. 10A;

FIG. 11A is a perspective view of one embodiment of a distal coupling member for the coupling system;

FIG. 11B is a front view of the distal coupling member of FIG. 11A;

FIG. 11C is a cross-sectional view of the distal coupling member of FIG. 11A;

Corresponding reference characters indicate corresponding elements among the view of the drawings. The headings used in the figures should not be interpreted to limit the scope of the claims.

DETAILED DESCRIPTION

Figure 3:
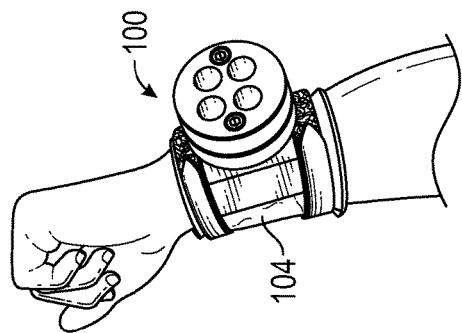
FIG. 3 is a front view of the coupling system of FIG. 1.
Figure 2:
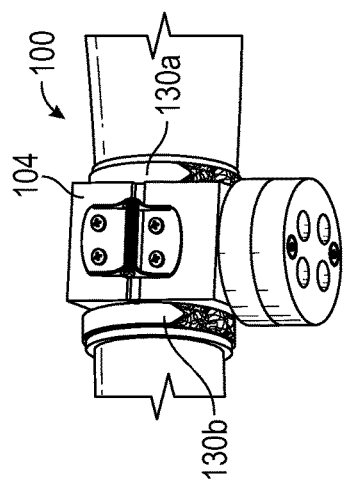
FIG. 2 is a bottom perspective image of a portion of the coupling system of FIG. 1.
Figure 4:
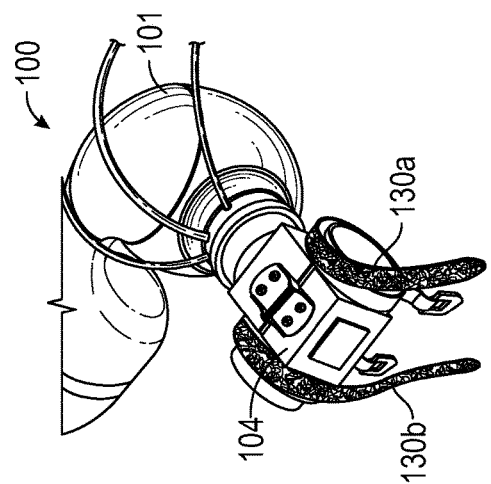
FIG. 4 is an image of the coupling system of FIG. 1 attached to a robotic arm.

Referring to the drawings, embodiments of a coupling system are illustrated and generally indicated as 100 in FIGS. 1-11 and 200 in FIGS. 15-20. In some embodiments, the coupling system 100 can be used in conjunction with a robotic device. For example, in one embodiment the coupling system 100 may be used to couple together an individual with a robotic arm 101. As best viewed in FIGS. 1-4, portions of the coupling system 100 can be operatively connected to both the individual and the robotic arm 101 so that movement can be transferred from the individual through the coupling system 100 (i.e., either from the robotic arm 101 to the individual or vice versa). In addition, in some embodiments, the coupling system 100 can be configured and arranged to physically separate should a sufficient force be applied to the coupling system 100 in an appropriate direction. As a result, the individual and the robotic arm 101 can physically separate should the need arise to prevent injury to the individual or to simply separate the individual and the robotic arm 101 when the individual has completed his or her tasks related to the robotic arm 101. Moreover, in some embodiments, the coupling system 100 can be configured to provide a comfortable interface for the individual so that the individual does not experience any significant pain or discomfort during use of the coupling system 100. It should be noted that the coupling system 100, although depicted as coupling together an arm of an individual with a robotic arm 101, can be used to couple other limbs of one or more individuals to other robotic devices. For example, the coupling system 100 can be used to couple a leg of an individual to another robotic device (e.g., a robotic leg or exoskeleton) (not shown).

In some embodiments, the coupling system 100 can include a coupling apparatus 102, as illustrated in FIGS. 5A-7. In particular, in some embodiments, the coupling apparatus 102 can include a brace member 104 engaged to a plurality of coupling members 106, 108, and 110. For example, the coupling apparatus 102 can include a proximal coupling member 106, coupled to a medial coupling member 108, which is coupled to a distal coupling member 110. In one embodiment, the proximal, medial, and distal coupling members 106, 108, and 110 can be arranged so that proximal coupling member 106 is the closest to the brace member 104 and the individual, while the distal coupling member 110 is closest to the robotic arm 101 and the medial coupling member 108 is positioned between the proximal and distal coupling members 106, 110. In one arrangement, as described in greater detail below, the proximal coupling member 106 may be coupled to the brace member 104 and the distal coupling member 110 may be coupled to the robotic arm 101.

In some embodiments, at least some portions of the coupling apparatus 102 can be formed from a metal-containing material. In one embodiment, at least some portions of the coupling apparatus 102 can be manufactured from a substantially or completely non-ferromagnetic material, such as aluminum. By way of example only, in one embodiment, at least some portions of the brace member 104 and the proximal, medial, and distal coupling members 106, 108, and 110 can be formed from aluminum using a conventional process, such as machining, casting, and/or molding. In other embodiments, the coupling apparatus 102 is formed from other materials, such as polymers or fiber-based materials (e.g., wood).

Figure 1:
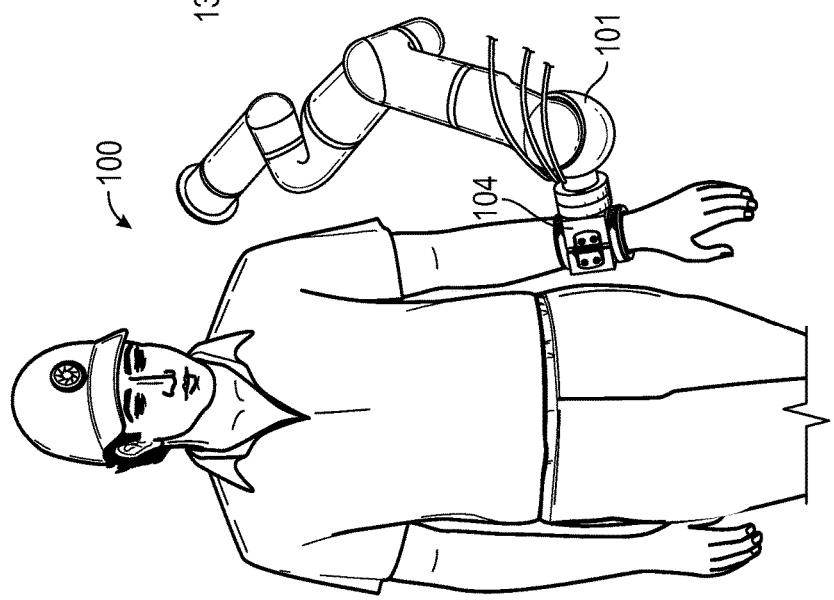
FIG. 1 is an image of an individual employing one embodiment of a coupling system.
Figure 5A:
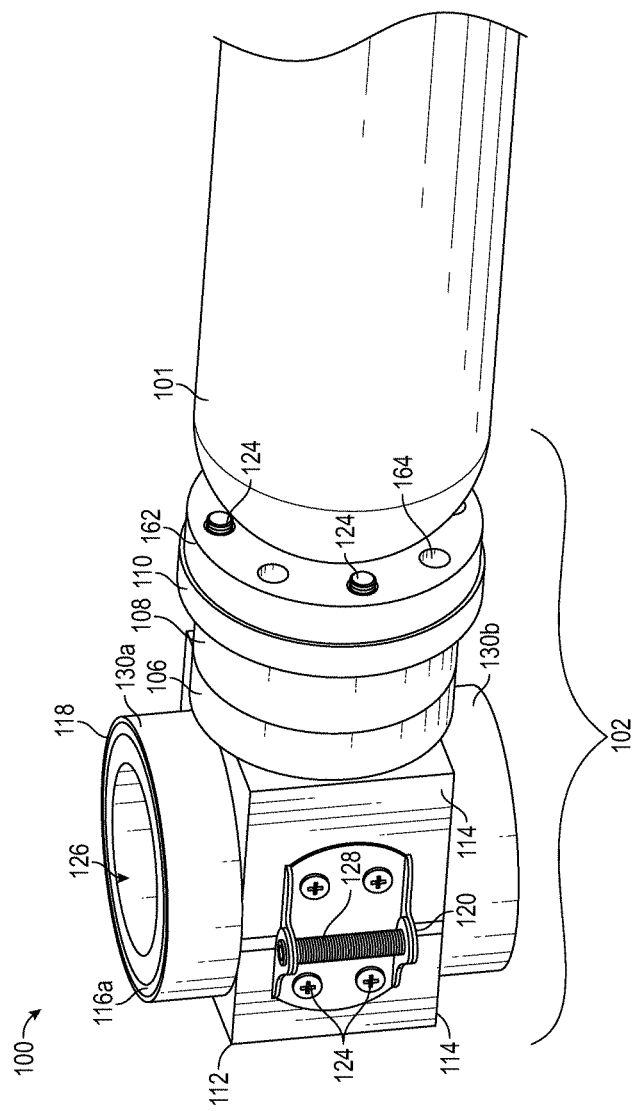
FIG. 5A is a first perspective view of one embodiment of a coupling system.

In one embodiment, the brace member 104 can be configured and arranged to receive at least a portion of the individual. For example, a portion of an upper extremity (e.g., a wrist) of the individual can be received with the brace member 104, as shown in FIG. 1. Referring now to FIGS. 6-8B, in one embodiment, the brace member 104 can be made from a plurality of subunits that can be coupled together in order to facilitate the positioning of the individual's wrist within the brace member 104. In one embodiment, the brace member 104 can be composed of a first portion 112 and a second portion 114.

In some embodiments, the first and second portions 112, 114 may be formed as similar components. For example, the first portion 112 of the brace member 104 may be formed with a first sleeve portion 116a and a second sleeve portion 116b, which both extend from opposing lateral sides of the first portion 112. Moreover, the second portion 114 of the brace member 104 may be formed with a third sleeve portion 118a and a fourth sleeve portion 118b, which both extend from opposing lateral sides of the second portion 114. In some embodiments, the first, second, third, and fourth sleeve portions 116a, 116b, 118a, and 118b may be substantially integral with the first and second portions 112, 114, respectively (e.g., the first and second sleeve portions 112, 114 can be manufactured with the first, second, third, and fourth sleeve portions 116a, 116b, 118a, and 118b). In other embodiments, one or more of the first, second, third, and fourth sleeve portions 116a, 116b, 118a, and 118b may be coupled to the first and second portions 112, 114, respectively, after manufacture of the first and second portions 112, 114.

In one embodiment, the first portion 112 and the second portion 114 are coupled together to collectively form the brace member 104. For example, the first and second portions 112, 114 may be movably coupled together using one or more hinge components 120. In particular, the first and second portions 112, 114 may each include one or more hinge apertures 122 that are configured and arranged to receive a coupling member 124 to retain together the brace member 104 and the hinge component 120. By way of example only, in one embodiment, the first portion 112 can include two coupling apertures 122 and the second portion 114 can include two coupling apertures 122. When the first and second portions 112, 114 of the brace member 104 are placed immediately adjacent to each other so that the coupling apertures 122 are proximate to each other, the hinge component 120 can be coupled to both of the first and second portions 112, 114 with a plurality of coupling members 124 (e.g., screws or bolts). As a result, after coupling of the hinge component 120 both the first and second portions 112, 114 of the brace member 104 can be retained together.

In some embodiments, once coupled together, the first and second portions 112, 114 can be configured to receive at least a portion of the individual. As previously mentioned, in some embodiments, the first and second portions 112, 114 may be formed to include a semi-circular configuration. As a result, when the first and second portions 112, 114 are coupled together, the semi-circular portions can be substantially or completely aligned to define at least a portion of a sleeve channel 126. In one embodiment, the first, second, third, and fourth sleeve portions 116a, 116b, 118a, and 118b may also align to form at least a portion of the sleeve channel 126. Specifically, the first and third sleeve portions 116a, 118a and the second and fourth sleeve portions 116b, 118b may align when the first and second portions 112, 114 are coupled together using the hinge component 120, thereby forming additional portions of the sleeve channel 126. As a result, the sleeve channel 126 can extend from a lateral edge of the first and third sleeve portions 116a, 118a to a lateral edge of the second and fourth sleeve portions 116b, 118b, thereby defining the sleeve channel 126 with a length sufficient to retain portions of the individual (e.g., the wrist) during operations of the robotic arm 101.

In some embodiments, the hinge component 120 can be configured to enable retention and removal of a portion of the individual from with the sleeve channel 126. For example, in one embodiment, the hinge component 120 includes one or more biasing members 128. In particular, each biasing member 128 can be configured and arranged to bias the brace member 104 in a substantially closed position (i.e., little or no space existing between the first portion 112 and the second portion 114 other than the sleeve channel 126). By way of example only, when the individual wishes to affix the brace member 104 to their body, the individual can exert a force on a side of the brace member 104 opposing the side of the brace member 104 to which the hinge component 120 is coupled. As a result, the brace member 104 can open to an extent that the individual can place a portion of their body within the sleeve channel 126. Moreover, the hinge component 126 can function as a pivot position during this opening process. Once the individual places the body part within the sleeve channel 126, the individual can slowly release the pressure exerted on the first and second portions 112, 114 and the biasing member 128 of the hinge component 120 can produce sufficient force to return the brace member 104 to substantially the same configuration as prior to insertion of the individual (i.e., in a closed position). In addition, the biasing member 128 can also exert a force to retain together the first and second portions 112, 114 during use of the coupling system 100 (i.e., the biasing member 128 can function to bias the brace member 104 in the closed position).

In some embodiments, the brace member 104 may include additional systems or components to retain portions of the individual within the sleeve channel 126. For example, as best seen in FIGS. 2, 4 and 5A-7, the brace member 104 includes one or more straps 130. In one embodiment, a first strap 130a is coupled to the first and third sleeve portions 116a, 118a (e.g., via an adhesive, such as an epoxy-based adhesive) and a second strap 130b is coupled to the second and third sleeve portions 116b, 118b (e.g., via an adhesive, such as an epoxy-based adhesive). By way of example only, the first and second straps 130a, 130b can operate in a substantially similar manner. Specifically, the first and second straps 130a, 130b can remain loose, uncinched, or unattached prior to and immediately after positioning a portion of individual within the sleeve channel 126. Shortly thereafter, the first and second straps 130a, 130b can be tightened or cinched to aid in retaining the individual within the brace member 104. For example, in one embodiment, the first and second straps 130a, 130b may include a fabric hook and loop-fastener arrangement (e.g., Velcro®) so that the first and second straps 130a, 130b can be locked together, respectively, to retain the brace member 104 during use of the coupling system 100.

In some embodiments, the brace member 104 can be configured to engage the first and second straps 130a, 130b. For example, in some aspects, one or more apertures (not shown) can be defined by an outer surface of the first, second, third, and/or fourth sleeve portions 116a, 116b, 118a, 118b to receive at least a portion of the first and second straps 130a, 130b, respectively. As such, the first and second straps 130a, 130b can be threaded through the apertures and retained in place. In other embodiments, other configurations of the first and second straps 130a, 130b (e.g., teeth-and-latch straps) can be coupled to the brace member 104, in a manner similar to coupling features on a snowboard or ski boots.

In some embodiments, the brace member 104 can be configured and arranged to provide a comfortable experience for the individual using the coupling system 100. In one embodiment, the brace member 104 includes a comfort member 132. Referring back to FIGS. 5A-7, in some embodiments, the comfort member 132 is at least partially positioned within the sleeve channel 126. When the individual positions a portion of his or her body within the brace member 104, the comfort member 132 can be positioned between the individual and the brace member 104. As previously mentioned, some portions of the coupling apparatus 102, which includes the brace member 104 may be fabricated from a metal-containing material. As a result, wearing of the brace member 104 may cause irritation, damage, or bruising of the skin of the individual during use of the coupling system 100. Accordingly, by including the comfort member 132, the risk of irritation, damage, bruising, and/or other discomfort can be at least partially reduced.

In some embodiments, the comfort member 132 can be manufactured from a material that is designed to cushion the portion of the individual within the brace member 104. For example, in some embodiments, the comfort member 132 can be made from a polyurethane material. In particular, the comfort member 132 can be made from a polyurethane material that has increased viscosity and density, relative to some conventional forms of polyurethane. By way of example only, in one embodiment, the comfort member 132 can be manufactured from conventional visco-elastic polyurethane foam (i.e., "memory foam").

Moreover, in addition to providing comfort, the inclusion of the comfort member 132 enables the use of the coupling system 100 by more than one individual. For example, some conventional coupling systems may be designed for a single individual with padding or cushioning that is contoured that the shape of that individual. However, by including the comfort member 132 within the sleeve channel 126, individuals with different contours and shapes can be accommodated within the brace member 104 because the comfort member 132 can receive body portions of different sizes. In addition, the first and second straps 130a, 130b can also be used to accommodate differently sized portions of different individuals. For example, should an individual with a large-diameter wrist position his or her wrist within the brace member 104, the comfort member 132 can be compressed to accommodate the larger diameter wrist and the first and second straps 130a, 130b can be used to ensure that the wrist stays securely within the brace member 104 during the use of the coupling system 100.

In some embodiments, the first and second portions 112, 114 are not necessarily completely identical, as illustrated in FIGS. 6-8B. For example, in one embodiment, the first portion 112 can include at least one arcuate, circuitous, or otherwise chamfered edge 134. Moreover, in one embodiment, the chamfered edge 134 can be on a side of the first portion 112 that opposes the side of the first portion 112 that includes the hinge apertures 122. Furthermore, in some embodiments, the second portion 114 can include an extension 136. In particular, the extension 136 can extend from the second portion 114 and may be configured and arranged to support and/or be coupled to other portions of the coupling apparatus 102. For example, in one embodiment, the extension 136 includes a plurality of receiving apertures 138 that can be configured and arranged to enable attachment of the proximal coupling member 106 to the brace member 104. In other embodiments, the proximal coupling member 106 can be coupled to the brace member 104 in other manners (e.g., welding, brazing, adhesives, etc.) or the proximal coupling member 106 and the brace member 104 can be integral with each other.

Referring now to FIGS. 5A-7 and 9A-9D, the proximal coupling member 106 may include a plurality of receptacles 140 and a plurality of coupling holes 142. For example, in one embodiment, the proximal coupling member 106 includes four receptacles 140 and two coupling holes 142. Specifically, the four receptacles 140 can be circumferentially arranged around a center of the proximal coupling member 106. In particular, the four receptacles 140 can be arranged so that a center of each receptacle 140 is spaced apart by about ninety degrees from a center of a circumferentially adjacent receptacle 140. However, in other embodiments, the proximal coupling member 106 can include greater or lesser numbers of receptacles 140. In addition, in some embodiments, one or more of the plurality of receptacles 140 do not extend through the proximal coupling member 106.

By way of example only, in one embodiment, the proximal coupling member 106 can include a first receptacle 140a, a second receptacle 140b, a third receptacle 140c, and a fourth receptacle 140d. Moreover, the plurality of receptacles 140 can be configured and arranged so that the first and third receptacles 140a, 140c and the second and fourth receptacles 140b, 140d are parallel with respect to each other. Specifically, the first and third receptacles 140a, 140c directly oppose each other (i.e., a center point of each of the first and third receptacles 140a, 140c is spaced apart by about one hundred eighty degrees). Similarly, the second and fourth receptacles 140b, 140d also directly oppose each other (i.e., a center point of each of the second and fourth receptacles 140b, 140d is spaced apart by about one hundred eighty degrees). As used herein, the term "parallel" refers to elements that directly oppose each other and are not circumferentially adjacent (e.g., the first and second receptacles 140a, 140b are not in a parallel orientation, but are rather circumferentially adjacent).

Referring now to FIGS. 5A-7 and 10A-10C, the medial coupling member 108 may include a similar configuration to the proximal coupling member 106. For example, the medial coupling member 108 defines a plurality of channels 144 and an additional plurality of coupling holes 142. In one embodiment, the plurality of channels 144 can be arranged in a manner substantially similar to the plurality of receptacles 142 of the proximal coupling member 106. Specifically, the medial coupling member 108 can include a first channel 144a, a second channel 144b, a third channel 144c, and a fourth channel 144d. In one embodiment, the first, second, third, and fourth channels 144a-144d can be circumferentially arranged around a center of the medial coupling member 108. In particular, the plurality of channels 144 can be arranged so that a center of each channel 144 is spaced apart by about ninety degrees from a center of a circumferentially adjacent channel 144. In addition, in some embodiments, one or more of the plurality of channels 144 extends through the medial coupling member 108. Moreover, similar to the plurality of receptacles 140a-140d, the first, second, third, and fourth channels 144a-144d are arranged in manner in which the first and third channels 144a, 144c and the second and fourth channels 144b, 144d are in a parallel configuration. However, in other embodiments, the medial coupling member 108 can include greater or lesser numbers of channels 144.

In one embodiment, one or more of the plurality of channels 144 can include a flange 146. Specifically, one or more of the plurality of channels 144 can be formed with a substantially cylindrical configuration that extends through the medial coupling member 108. In one embodiment, a flange 146 can extend radially inward from a circumference of each of the plurality of channels 144. For example, the medial coupling member 108 can include a proximal face 148 and a distal face 150, with the proximal face 148 being positioned adjacent to the proximal coupling member 106 and the distal face 150 being position adjacent to the distal coupling member 110. In one embodiment, the flanges 146 can be positioned within each plurality of channels 144 at a position more adjacent to the proximal face 148 than the distal face 150. As a result, a diameter of each of the channels 144 can be narrowed at the flange 146, relative to other portions of the plurality of channels 144 (e.g., a position more adjacent to the distal face 150).

In some embodiments, the proximal and medial coupling members 106, 108 are coupled to the brace member 104 (i.e., the extension 134) so that the plurality of receptacles 140, plurality of coupling holes 142, and plurality of channels 144 are substantially aligned relative to each other. More specifically, the proximal and medial coupling members 106, 108 can be positioned so that the first, second third, and fourth receptacles 140a-140d are aligned with the first, second, third, and fourth channels 144a-144d, respectively. Moreover, the proximal and medial coupling members 106, 108 can be positioned so that the coupling holes 142 are aligned with the receiving apertures 138 of the second portion 114. As a result, one or more coupling members 124 can be inserted through the coupling holes 142 and receiving apertures 138 to retain together the brace member 104, the proximal coupling member 106, and the medial coupling member 108. For example, one or more screws or bolts can be used to couple together (e.g., reversible or irreversibly) the brace member 104, the proximal coupling member 106, and the medial coupling member 108.

In one embodiment, prior to or after coupling together the brace member 104, the proximal coupling member 106, and the medial coupling member 108, one or more magnetic bodies 152 can be positioned within at least some of the plurality of receptacles 140a-140d and/or the plurality of channels 144a-144d. Specifically, one or more of the magnetic bodies 152 are placed in parallel-oriented receptacles 140a-140d and/or parallel-oriented channels 144a-144d. By way of example only, in one embodiment, a magnetic body 152 can be placed in the first channel 144a in a position immediately adjacent to the flange 146 and another magnetic body 152 can be placed in the third channel 144c immediately adjacent to the flange 146. In other embodiments, the magnetic body 152 can be placed in the second channel 144b in a position immediately adjacent to the flange 146 and another magnetic body 152 can be placed in the fourth channel 144d immediately adjacent to the flange 146. In some embodiments, the flanges 146 can be configured and arranged to engage a portion of the magnetic bodies 152, thereby retaining the magnetic bodies 152 within the medial coupling member 108.

In addition, in other embodiments, the magnetic bodies 152 can be placed in each of the plurality of channels 144a-144d. Specifically, a magnetic body 152 can be placed in each of the first, second, third, and fourth channels 144a-144d at positions immediately adjacent to the flanges 146. Moreover, in some embodiments, as long as one magnetic body 152 is positioned within each of two parallel-oriented channels 144 or receptacles 140, additional magnetic bodies 152 can be positioned in the circumferentially adjacent channels 144 or receptacles 140. By way of example only, magnetic bodies 152 may be positioned within the first and third channels 144a, 144c (i.e., two parallel-oriented channels 144) and additional magnetic bodies 152 can be positioned within one or both of the second and fourth channels 144b, 144d (i.e., channels 144 that are circumferentially adjacent). Moreover, as previously mentioned, the magnetic bodies 152 can also be disposed within the plurality of receptacles 140a-140d in similar patterns.

In some embodiments, the magnetic bodies 152 can be manufactured from any kind of ferromagnetic material that can be shaped to fit within the plurality of channels 144 and/or the plurality of receptacles 140. By way of example only, in some embodiments, the magnetic bodies 152 can be manufactured from neodymium or other rare-earth magnetic materials.

In other embodiments, the magnetic bodies 152 can be manufactured as electromagnets or other structures or apparatuses capable of generating a magnetic field. For example, the coupling system 100 can function with one or more of the magnetic bodies 152 replaced by an electromagnet (not shown). As such, an individual employing the coupling system 100 can relatively easily and precisely control the coupling force (i.e., the magnetic field generated by the electromagnet). In particular, the individual using the coupling system 100 could vary the current supplied to the electromagnet to vary the magnetic field generated by the electromagnet, and correspondingly, vary the coupling force. Moreover, individuals using embodiments of the coupling system 100 that include one or more electromagnets can vary the coupling force before, during, or after use of the coupling system 100.

In some embodiments, by including one or more electromagnets in the coupling system 100, additional features can be included with the coupling system 100. For example, in some embodiments, the coupling system 100 can include a first killswitch (not shown). In some aspects, the first killswitch can function as a device that receives an input from the robotic arm 101, processes the input, and accordingly affects the coupling status of the coupling system 100. For example, the first killswitch can receive an input indicating that the robotic arm 101 has malfunctioned or is otherwise disabled after the individual is coupled to the robotic arm 101, as described in greater detail below. As such, the first killswitch can cease current from flowing to the electromagnet to uncouple the individual and the robotic arm 101 to prevent any kind of potential injury to the individual.

Referring now to FIGS. 6, 7, and 11A-11C, in some embodiments, the distal coupling member 110 may include a plurality of pegs 154 and an additional plurality of coupling holes 142. In some embodiments, the plurality of pegs 154 can be can be arranged in a manner substantially similar to the plurality of receptacles 142 of the proximal coupling member 106 and the plurality of channels 144 of the medial coupling member 108. Specifically, the distal coupling member 110 can include a first peg 154a, a second peg 154b, a third peg 154c, and a fourth peg 154d. In one embodiment, the first, second, third, and fourth pegs 154a-154d can be circumferentially arranged around a center of the distal coupling member 110. In particular, the plurality of pegs 154 can be arranged so that a center of each peg 154 is spaced apart by about ninety degrees from a center of a circumferentially adjacent peg 154. Moreover, similar to the plurality of receptacles 140a-140d and the plurality of channels 144a-144d, the first, second, third, and fourth pegs 154a-154d can be arranged in manner in which the first and third pegs 154a, 154c and the second and fourth pegs 154b, 154d are in a parallel configuration.

In some embodiments, the distal coupling member 110 includes a proximal face 156 and a distal face 158. More specifically, the proximal face 156 can be positioned adjacent to the medial coupling member 108 and the distal face 158 can be positioned more adjacent to the robotic arm 101. In one embodiment, one or more of the plurality of pegs 154 extends from the proximal face 156 of the distal coupling member 110. By way of example only, in one embodiment, each of the plurality of pegs 154 can extend from the proximal face 156 a distance of about one-half inch. However, in other embodiments, at least some of the plurality of pegs 154 may extend other distances from the proximal face 156. In addition, as discussed in greater detail below, the plurality of pegs 154 can be at least partially received within the plurality of channels 144 to aid in retaining together the coupling apparatus 102.

Figure 12:
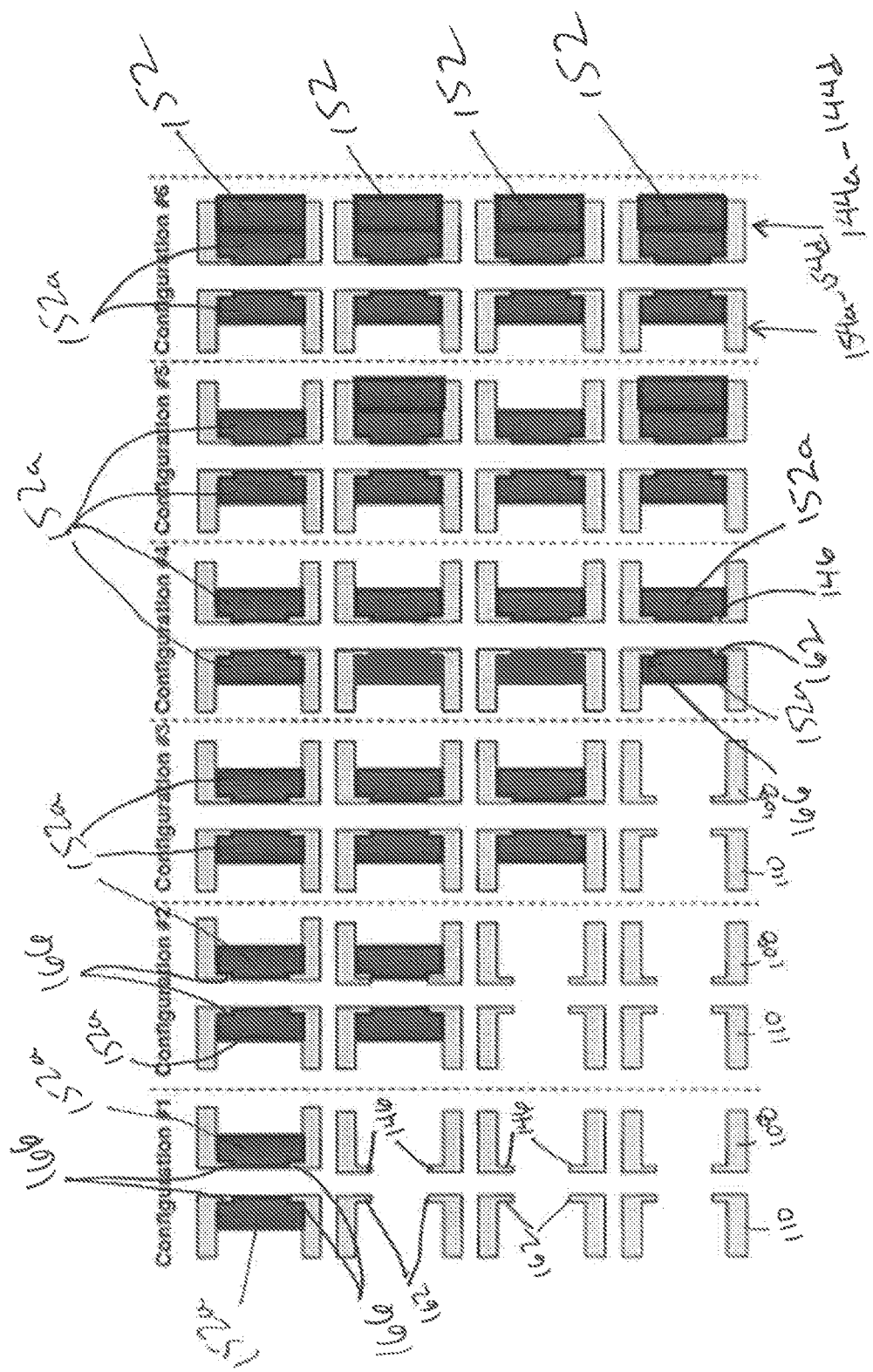
FIG. 12 is a simplified diagram of six different experimental configurations of magnetic bodies used to test the adaptive characteristics of the coupling system of FIG. 1.

In some embodiments, one or more of the plurality of pegs 154 can be configured and arranged to receive one or more magnetic bodies 152. Specifically, the magnetic bodies 152 and the plurality of pegs 154 can each include a similar diameter such that one or more of the magnetic bodies 152 can be positioned within one or more of the plurality of pegs 154. In other words, the plurality of pegs 154 can define a substantially hollow configuration so that the magnetic bodies 152 may be disposed inside of the plurality of pegs 154. Moreover, in one embodiment, one or more of the plurality of pegs 154 can include a peg flange 160 to aid in retaining the magnetic bodies 152. For example, similar to the plurality of channels 144, the plurality of pegs 154 may also be formed in a substantially cylindrical configuration and the peg flanges 160 can extend radially inward from the circumference of the plurality of pegs 154. By way of example only, in one embodiment, the magnetic bodies 152 can be positioned within the plurality of pegs 154 via insertion into the plurality of pegs 154 through the distal face 158 of the distal coupling member 110. The magnetic bodies 152 can be disposed adjacent to the peg flanges 160, which can engage a portion of the magnetic bodies 152 (i.e., a shoulder recess 166, as shown in FIG. 12) to retain the magnetic bodies 152 within the plurality of pegs 154.

In some embodiments, the magnetic bodies 152 can be positioned within the plurality of pegs 154 in a manner similar to the one in which the magnetic bodies 152 are positioned within the plurality of channels 144 and/or the plurality of receptacles 140. Specifically, one or more of the magnetic bodies 152 are placed in parallel-oriented pegs 154a-154d. By way of example only, in one embodiment, a magnetic body 152 can be placed in the first peg 154a in a position immediately adjacent to the peg flange 160 and another magnetic body 152 can be placed in the third peg 154c immediately adjacent to the peg flange 160. In other embodiments, the magnetic body 152 can be placed in the second peg 154b in a position immediately adjacent to the peg flange 160 and another magnetic body 152 can be placed in the fourth peg 154d immediately adjacent to the peg flange 160.

In addition, in other embodiments, the magnetic bodies 152 can be placed in each of the plurality of pegs 154a-154d. Specifically, a magnetic body 152 can be placed in each of the first, second, third, and fourth pegs 154a-154d at positions immediately adjacent to the peg flanges 160. Moreover, in some embodiments, as long as one magnetic body 152 is disposed within each of two parallel-oriented pegs 154, additional magnetic bodies 152 can be positioned in the circumferentially adjacent pegs 154. By way of example only, magnetic bodies 152 may be positioned within the first and third pegs 154a, 154c (i.e., two parallel-oriented pegs 154) and additional magnetic bodies 152 can be positioned within one or both of the second and third pegs 154b, 154d (i.e., pegs 154 that are circumferentially adjacent).

In addition, the positioning of the magnetic bodies 152 within the plurality of channels 144 and/or the receptacles 140 can impact the positioning of the magnetic bodies 152 within the plurality of pegs 154. For example, attraction between the magnetic bodies 152 in the plurality of pegs 154 and the plurality of channels 144 can at least partially provide for the coupling force to retain together the individual and the robotic arm 101. Accordingly, in order to provide the coupling force, the magnetic bodies 152 should be in the plurality of pegs 154 and the plurality of channels 144 that align upon assembly of the coupling apparatus 102. For example, the first, second, third, and fourth pegs 154a-154d can be received within the first, second, third, and fourth channels 144a-144d, respectively. In order to provide magnetic attraction to retain together the coupling apparatus 102, the magnetic bodies 152 should be in similar positions. By way of example only, one or more magnetic bodies 152 can be positioned in the first and third pegs 154a, 154c and the first and third channels 144a, 144c so that the magnetic bodies 152 are immediately adjacent to each other when the medial and distal coupling members 108, 110 are positioned adjacent to each other to provide the attractive force to retain together the coupling apparatus 102.

As previously mentioned, in some embodiments, the coupling system 100 can include different numbers of receptacles 140, channels 144, and pegs 154. The arrangement of the plurality of magnetic bodies 152 can be at least partially impacted to accommodate the configuration. By way of example only, in some embodiments, the coupling system 100 includes an odd number of receptacles 140, channels 144, and pegs 154 (e.g., three, five, seven, etc.). As a result, to provide balance between the elements of the coupling apparatus 102, at least one magnetic body 152 is placed in each of the receptacles 140, channels 144, and pegs 154. Moreover, when the coupling system 100 includes an odd number of receptacles 140, channels 144, and pegs 154, the magnetic bodies 152 need not be placed in receptacles 140, channels 144, and pegs 154 that are parallel with respect to each other.

Figure 6:
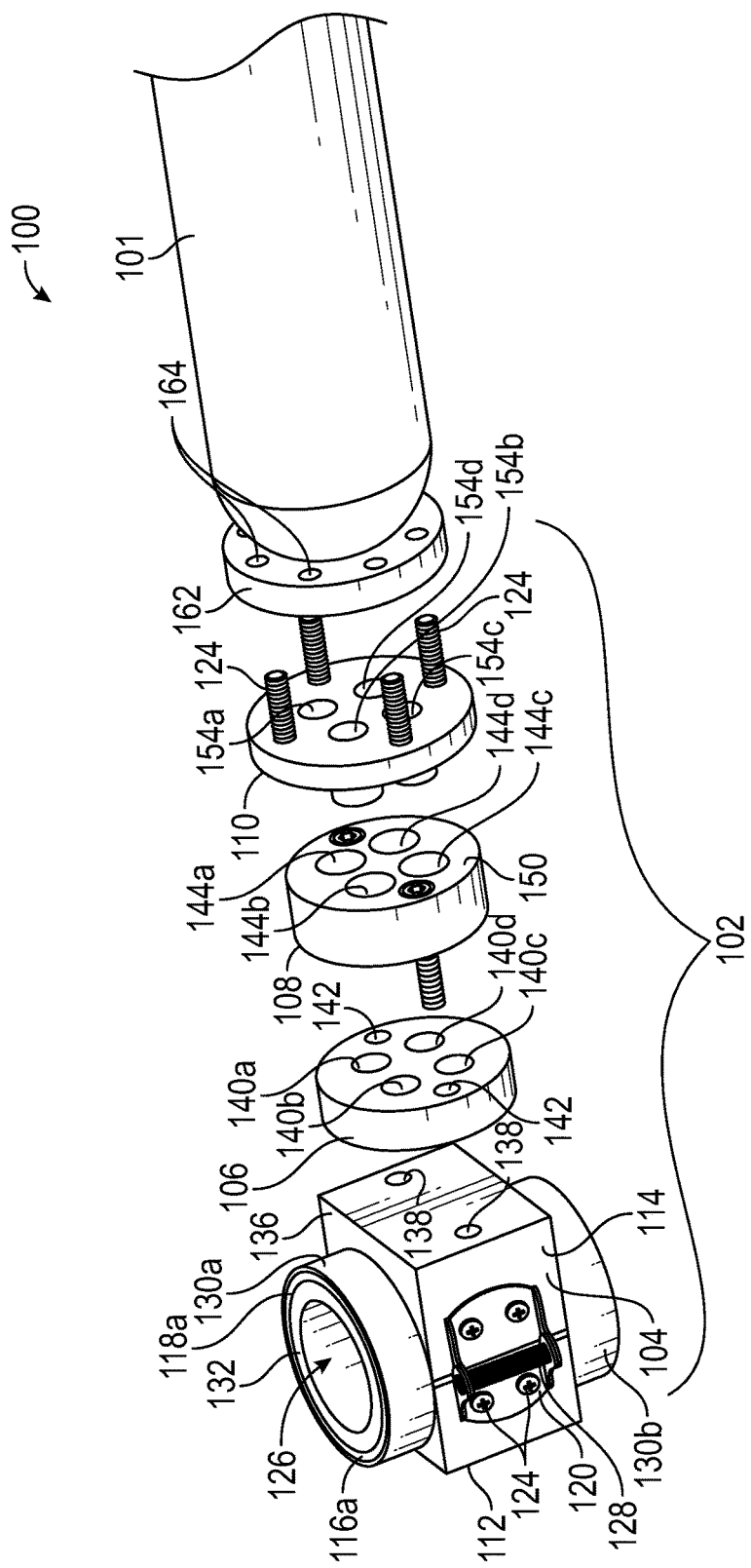
FIG. 6 is a first exploded perspective view of one embodiment of a coupling system.
Figure 7:
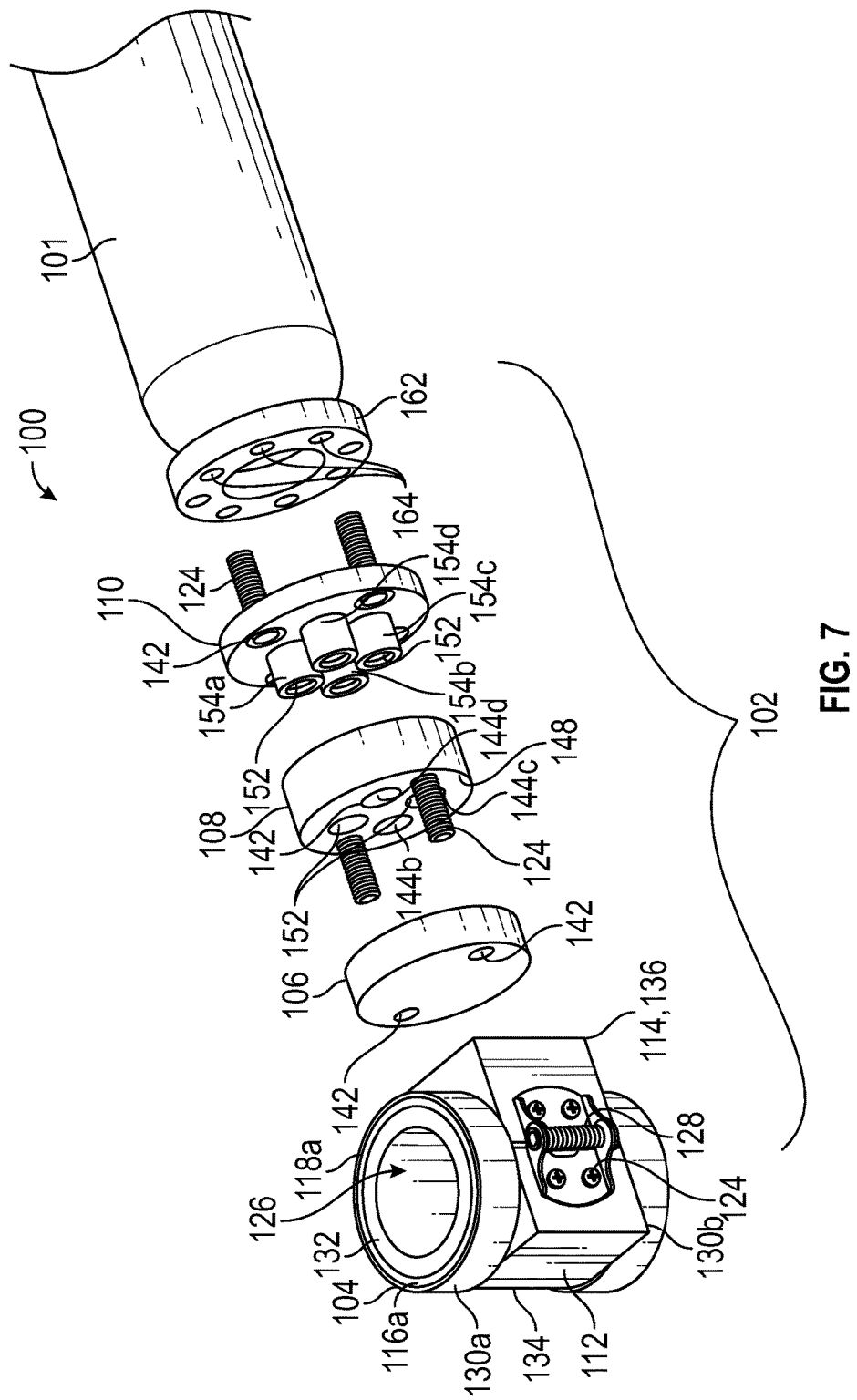
FIG. 7 is a second exploded perspective view of the coupling system of FIG. 6.
Figure 8B:
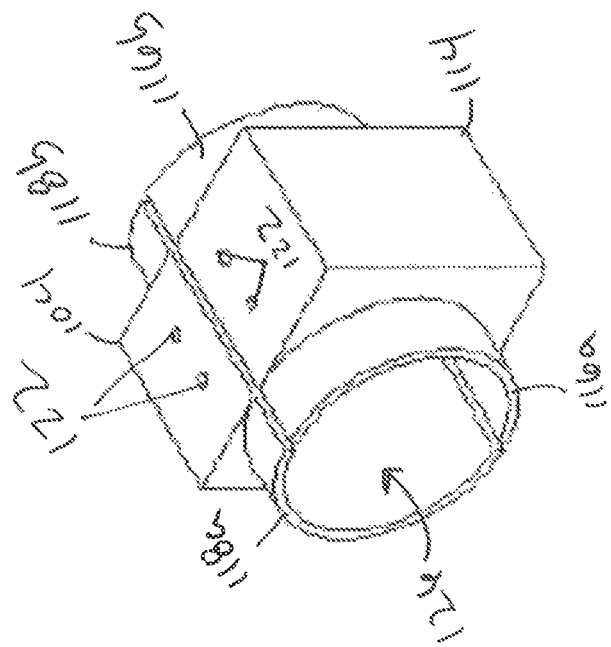
FIG. 8B is a perspective view of the brace member of FIG. 8A.
Figure 8A:
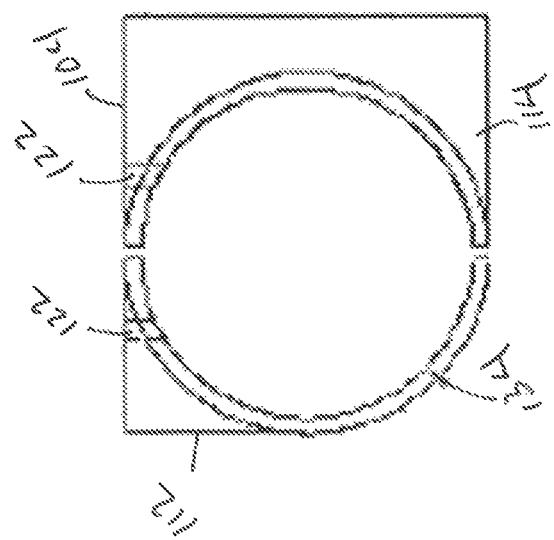
FIG. 8A is a side view of one embodiment of a brace member for the coupling system.
Figure 9B:
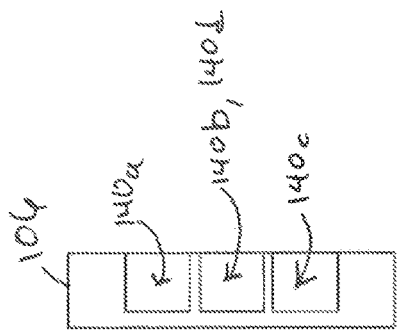
FIG. 9B is a front view of the proximal coupling member of FIG. 9A.
Figure 9C:
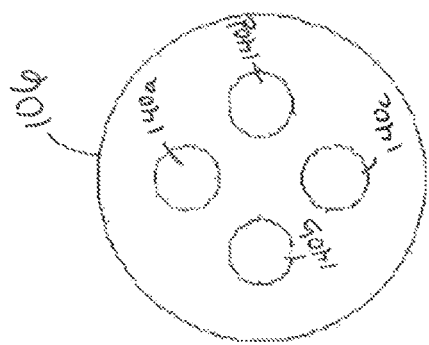
FIG. 9C is a cross-sectional view of the proximal coupling member of FIG. 9A.
Figure 9A:
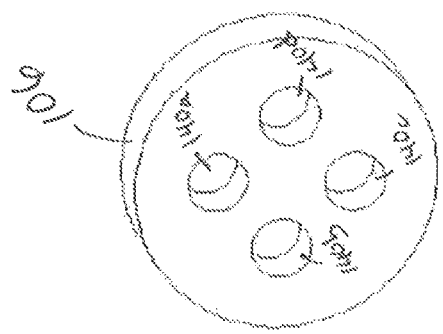
FIG. 9A is a perspective view of one embodiment of a proximal coupling member for the coupling system.

As shown in FIGS. 6 and 12, the magnetic bodies 152 can be provided in one or more configurations. For example, at least some of the magnetic bodies 152 can be configured as "step-out" magnetic bodies 152a. In particular, the step-out magnetic bodies 152a can be configured to engage one or more of the flanges 146 and/or one or more of the peg flanges 160. Specifically, some or all of the step-out magnetic bodies 152a can include a shoulder recess 166 that is configured and arranged to engage one or more of the flanges 146 and/or one or more of the peg flanges 160 of the medial and distal coupling members 108, 110, respectively. Moreover, in some aspects, at least a portion of the magnetic bodies 152 can include a substantially uniform or "straight" configuration such that the magnetic bodies 152 do not include a shoulder recess 166. In some embodiments, the step-out magnetic bodies 152a can be first placed within one or more of the plurality of channels 144a-144d to engage the flanges 146 or the plurality of pegs 154a-154d to engage the peg flanges 160 and the straight configured magnetic bodies 152 can be used thereafter to provide magnetic force, as determined by the user.

In some embodiments, the coupling system 100 can include configurations that can enable variations in the magnetic field generated by the magnetic bodies 152. In some aspects, the coupling system 100 can be configured such that the coupling apparatus 102 includes variable distance permanent magnets. For example, some or all of the plurality of receptacles 140, the plurality of channels 144, and/or the plurality of pegs 154 that include one or more magnetic bodies 152 can also include an apparatus (not shown) to move the magnetic bodies 152 in a generally linear direction. Specifically, some or all of the plurality of receptacles 140, the plurality of channels 144, and/or the plurality of pegs 154 can include a track (not shown) (e.g., a screw or axle) that be positioned adjacent to the magnetic bodies 152. As such, the individual using the coupling system 100 can activate and deactivate the apparatus to cause some or all of the magnetic bodies 152 in the coupling system 100 to either move a greater distance apart or a greater distance together. As a result, when the apparatus causes the magnetic bodies 152 to move closer together, the coupling or attractive force of the magnetic bodies 152 increases. Conversely, when the apparatus causes the magnetic bodies 152 to move a greater distance apart, the coupling or attractive force of the magnetic bodies 152 decreases, thereby providing adjustability of the magnetic forces of the coupling system 100.

In some embodiments, the coupling system 100 can include a connector plate 162. Specifically, the connector plate 162 can be configured and arranged to couple the distal coupling member 110 to the robotic arm 101. For example, a plurality of receiving holes 164 are circumferentially arranged around at least a portion of a diameter of the connector plate 162. As a result, the plurality of coupling holes 142 through the distal coupling member 110 can be substantially aligned with at least a portion of the plurality of receiving holes 164 through the connector plate 162 so that one or more coupling members 124 can be disposed therethrough to retain the distal coupling member 110 and the connector plate 162 with respect to the robotic arm 101.

In some embodiments, elements of the coupling system 100 can be retained in position in other manners. For example, in lieu of, or in addition to a plurality of coupling holes 142 and a plurality of coupling members 124, some embodiments of the coupling system 100 include a coupling mechanism (not shown). In some embodiments, the coupling mechanism can be configured as a latch and/or a hinge that can retain together the brace member 104, the proximal, medial, and distal coupling members 106, 108, 110, and/or the robotic arm 101. Moreover, the coupling mechanism can be configured to enable relatively easy access to the magnetic bodies 152 without the need to remove the coupling members 124.

As a result of some of the previously mentioned configurations, the coupling system 100 can provide an individual-robot interface. By way of example only, after positioning the magnetic bodies 152 within some or all of the plurality of pegs 154, the distal coupling member 110 and the connector plate 162 are reversibly or irreversibly coupled to the robotic arm 101. Moreover, after positioning the magnetic bodies 152 within the corresponding plurality of channels 144 or the corresponding plurality of receptacles 140, the medial and proximal coupling members 106, 108 may be coupled to the brace member 104. For example, the magnetic bodies 152 are placed within parallel-oriented pegs 154 (e.g., the first and third pegs 154a, 154c) and parallel-oriented channels 144 (e.g., the first and third channels 144a, 144c).

Once the individual is ready to use the robotic arm 101, the individual can affix the brace member 104 to a portion of his or her body. For example, the individual can affix the brace member 104 to his or her wrist. Once the wrist is positioned within the sleeve channel 126 and substantially protected by the comfort member 132, the first and second straps 130a, 130b can be tightened and/or attached together to retain the wrist within the brace member 104. At this point, the individual can position the brace member 104, proximal coupling member 106, and medial coupling member 108 at a position adjacent to the robotic arm 101 and the distal coupling member 110. Specifically, the medial coupling member 108 can be positioned so that the plurality of pegs 154 are received within the corresponding plurality of channels 144, thereby introducing the magnetic bodies 152 within the parallel-oriented pegs 154 and the magnetic bodies 152 within the parallel-oriented channels 144. As a result of the close proximity of the magnetic bodies 152 producing magnetic attraction, the plurality of pegs 154 are retained within the plurality of channels 144, and the coupling apparatus 102 is retained as a single unit. The individual is then free to move the robotic arm 101 or vice versa.

The above configurations provide significant benefits over conventional configurations. Many conventional systems require attachment between the individual and the robotic system at multiple points, such as at the upper arm, the wrist, the shoulder, and the hand. The single-point attachment feature of the coupling system 100 (e.g., attachment at the wrist of the individual) enables easier use of the coupling system 100 and more freedom of movement. In addition, the engagement of the plurality of pegs 154 within the plurality of channels 144 enables forces (torque) to be transferred in any direction. Specifically, after positioning the plurality of pegs 154 within the plurality of channels 144, force can be transferred from the individual to the robotic arm 101 in any direction without a concern for inadvertent separation of the medial and distal coupling members 108, 110, as long as the force in certain directions does not exceed the force necessary to overcome the attraction between the magnetic bodies 152.

Additionally, by being coupled at the wrist, the coupling system 100 enables hands-free usage. In particular, many conventional coupling systems require that the hands of the individual be used in retaining the connection between the individual and the robotic arm 101. This configuration of the coupling system 100 therefore enables the use of the hands for any other necessary tasks while force is being exchanged between the brace member 104 and the robotic arm 101.

Significantly, the coupling system 100 can disengage the individual from the robotic arm 101 upon the proper application of force. Many conventional systems require that the individual be strapped, buckled, or otherwise secured to the conventional coupling system. Moreover, such a conventional coupling system must be solidly screwed, welded, or otherwise attached to the robot. This conventional configuration could give rise to significant injury upon malfunction of the robot because the individual cannot readily disengage from the robot.

In some embodiments of the coupling system 100, the application of a force in particular directions can overcome the magnetic attraction of the magnetic bodies 152 and can be sufficient to uncouple or disengage the individual from the robotic arm 101. For example, if the individual wishes to disengage from the robotic arm 101, the individual may apply a magnitude of force in a direction parallel to the plurality of pegs 154 and/or the plurality of channels 144 that is sufficient to overcome the magnetic coupling between the distal coupling member 110 and the medial coupling member 108. As a result, should the need arise (e.g., due to an emergency), the individual can disengage from the robotic arm 101.

Some embodiments of the coupling system 100 can include a second killswitch (not shown) that is configured to at least partially function when the individual disengages the robotic arm 101. For example, the second killswitch can be in communication with a power source of the robotic arm 101 and can be configured to sense the coupling status of the coupling system 100. In particular, if the individual using the coupling system 100 is required to disengage from the robotic arm 101 (e.g., due to a malfunction), the second killswitch can function to deactivate the power supply of the robotic arm 101. In some aspects, the second killswitch can be configured as a circuit that bridges a gap between the medial and distal coupling members 108, 110 so that when the uncoupling event occurs, the separation is detected by the second killswitch and the power flow to the robotic arm 101 is severed by the second killswitch. As a result, if the robotic arm 101 malfunctions, the individual using the coupling system 100 can not only disengage from the robotic arm 101, but can also ensure that the robotic arm 101 ceases operating upon disengagement. In addition, in some embodiments, the second killswitch can be used activate the robotic arm 101. In particular, the second killswitch can function as a safety device such that the robotic arm 101 is not able to function until the coupling apparatus 102 is coupled to the robotic arm 101.

In some embodiments, the coupling system 100 can be customizable for use with different applications. For example, to produce a greater amount of magnetic attraction, more than one magnetic body 152 can be used in the plurality of channels 144 and/or the plurality of pegs 154. Additional magnetic bodies 152 can be added to increase the magnitude of force necessary to separate the medial and distal coupling members 108, 110. By way of example only, in some embodiments, if a magnetic body 152 is positioned within each of the first and third channels 144a, 144c and the first and third pegs 154a, 154c, then additional magnetic bodies 152 can be added to one or more of the first and third channels 144a, 144c and the first and third pegs 154a, 154c to increase the magnetic forces. Specifically, the additional magnetic bodies 152 can be added in series (i.e., one magnetic body 152 behind the first magnetic body 152). In some embodiments, each of the plurality of channels 144 and/or each of the plurality of pegs 154 can be configured to receive up to five magnetic bodies 152, depending on the size and thickness of the magnetic bodies 152. In addition, as previously mentioned, additional magnetic bodies 152 can be positioned within all of the plurality of channels 144 and/or all of the plurality of pegs 154 to produce greater amounts of magnetic force. As a result, the magnetic force necessary to accomplish a desired result can be provided by customizing the number, size, and arrangement of the magnetic bodies 152 within the plurality of channels 144 and/or the plurality of pegs 154. Accordingly, the coupling system 100 can be customized for applications in which a greater separation force is desired (e.g., augmentative applications) as well as applications in which a lesser separation force is desired (e.g., rehabilitation applications).

In addition, the customization of the coupling system 100 can be further influenced by other parameters. For example, the velocity with which the individual pulls the coupling apparatus 102 away from the robotic arm 101 influences the force necessary to separate the distal and medial coupling members 108, 110. Specifically, the graphs illustrate that the greater velocity with which the individual exerts the force to overcome the attractive forces of the magnetic bodies 152, the less force is necessary to pull apart the coupling apparatus 102. As a result, when customizing the coupling system 100 for a given application, the velocity at which the individual will be moving his or her appendages (e.g., wrist) may influence the design of the coupling system 100. For example, for applications in which the wrist may be moving at greater velocities, greater numbers of magnetic bodies 152 may be used to ensure that the coupling apparatus 102 does not separate during use. Conversely, applications where the wrist may be moving at lesser velocities, a fewer number of magnetic bodies 152 may be used so that individual can separate from the robotic arm 101 without having to exert too great of a force to affect separation of the coupling apparatus 102.

Figure 15:
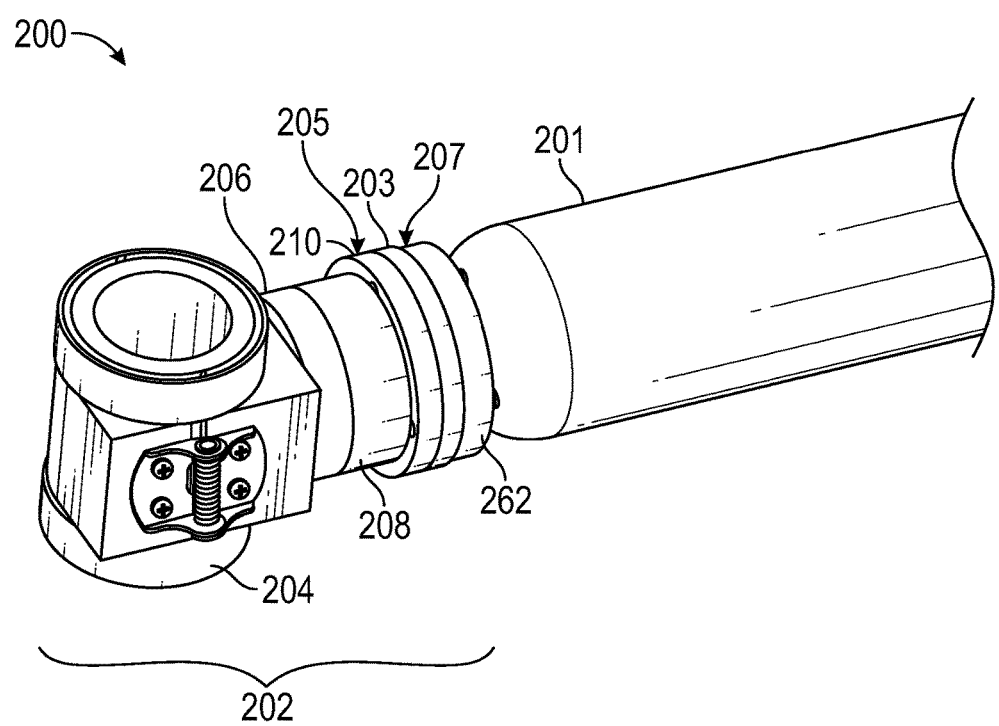
FIG. 15 is a first perspective view of a second embodiment of the coupling system.
Figure 16:
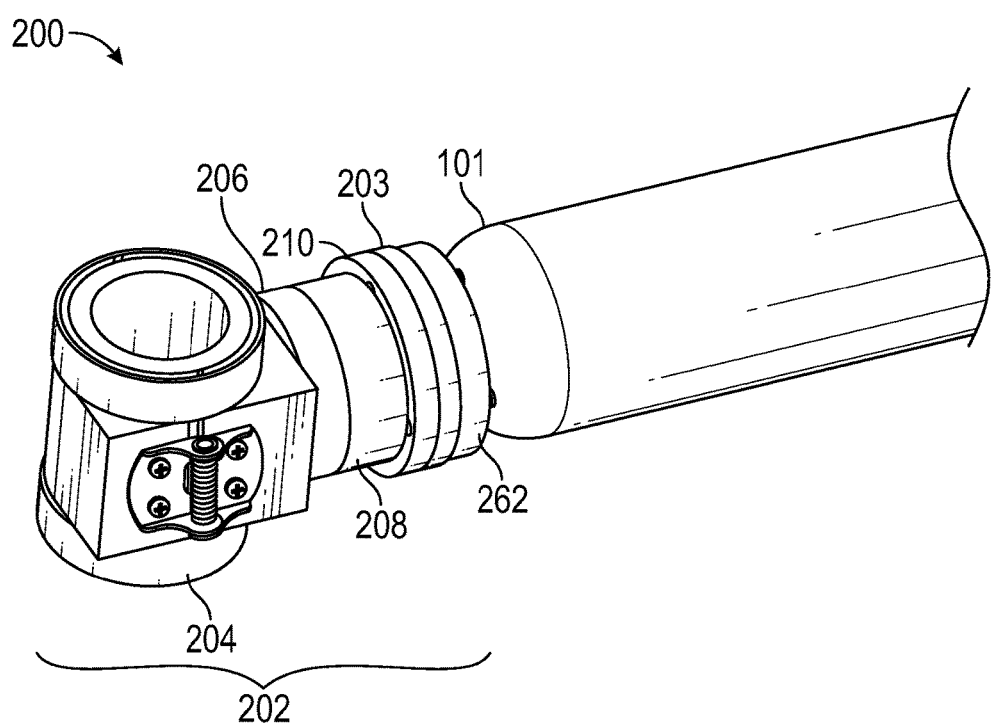
FIG. 16 is a second perspective view of the coupling system of FIG. 15.

FIGS. 15 and 16 illustrate another embodiment of the coupling system 200. The coupling system 200 may be provided in a substantially similar configuration to other embodiments, but can be configured for improved positioning of the plurality of magnetic bodies 254 (not shown in FIGS. 15 and 16). For example, the coupling system 200 can include the coupling apparatus 202, which may further include the brace member 204 and the proximal, medial, and distal coupling members 206, 208, 210. Moreover, the coupling apparatus 202 may also be configured and arranged to engage the robotic arm 201. As such, the coupling system 200 may be used in a manner similar to other embodiments.

Figure 19:
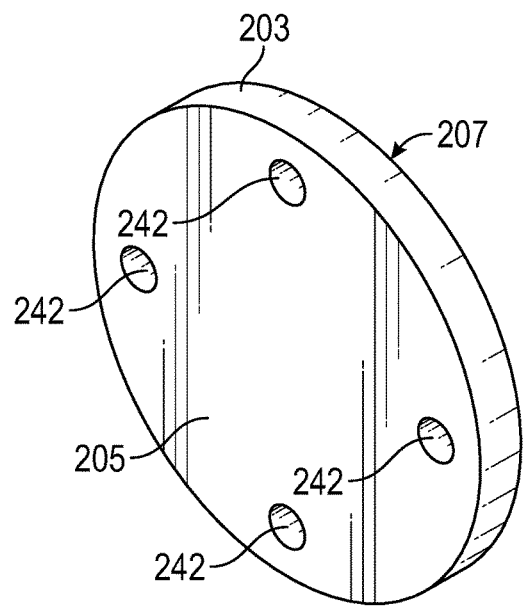
FIG. 19 is a perspective view of a backing plate.
Figure 20:
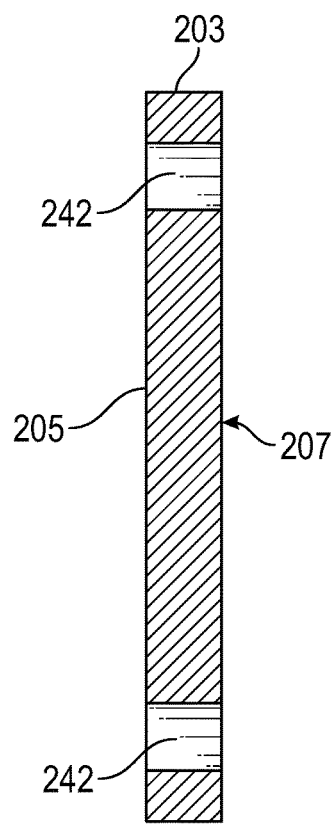
FIG. 20 is a cross-sectional view of the backing plate of FIG. 19.

In some aspects, the coupling system 200 can include a backing plate 203. As illustrated in FIGS. 15, 16, 19, and 20, the backing plate 203 can be provided in a substantially circular configuration and a size that is substantially similar to the proximal, medial, and distal coupling members 206, 208, 210. As illustrated in FIGS. 19 and 20, the backing plate 203 can include a plurality of coupling holes 242 that are configured and arranged to receive one or more coupling members (not shown). In addition, the backing plate 203 can define a proximal face 205 and a distal face 207 such that when the coupling apparatus 202 is assembled, the proximal face 205 can be positioned substantially adjacent to the distal coupling member 210 and the distal face 207 can be positioned substantially adjacent to the connector plate 262.

Figure 17:
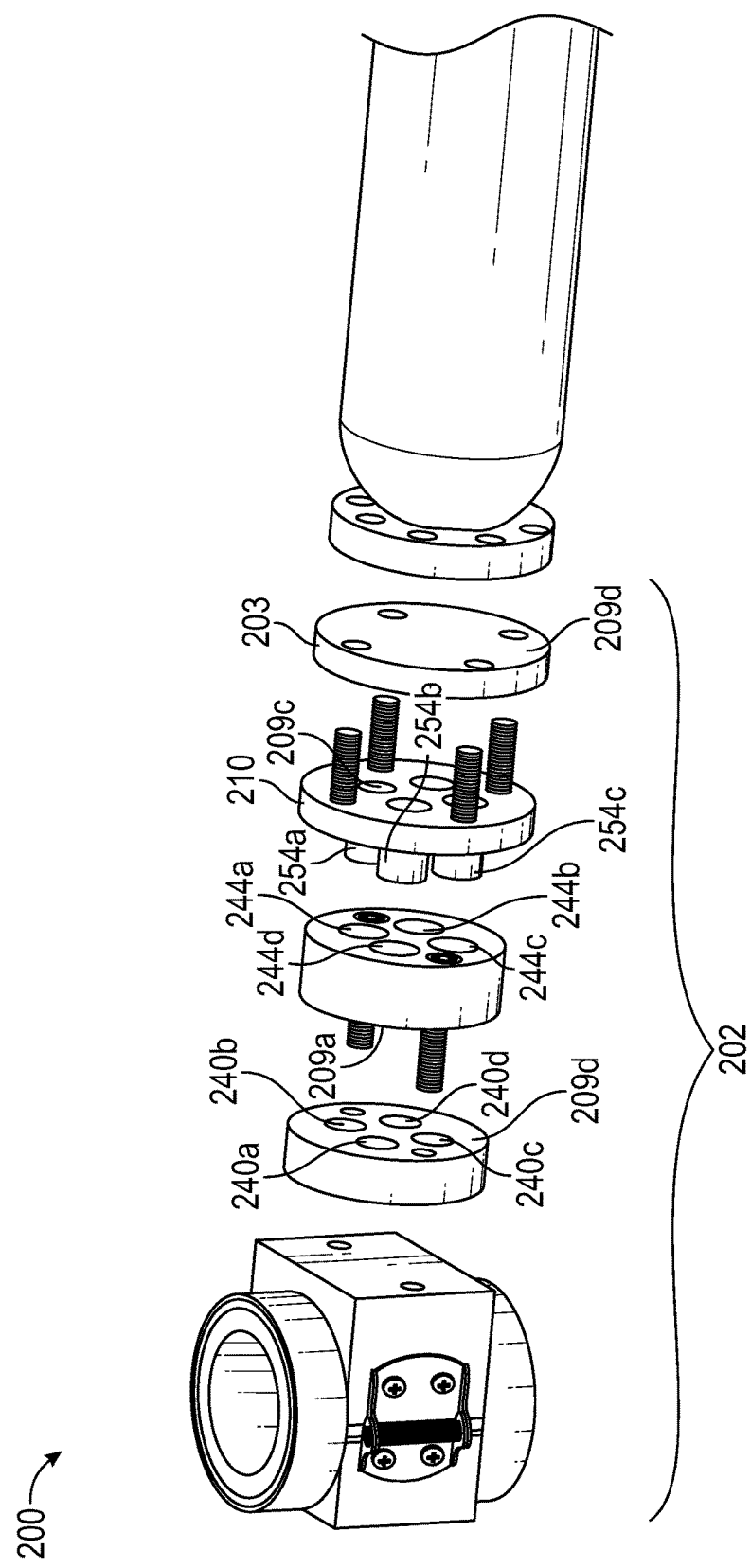
FIG. 17 is a first exploded perspective view of the coupling system of FIG. 15.
Figure 18:
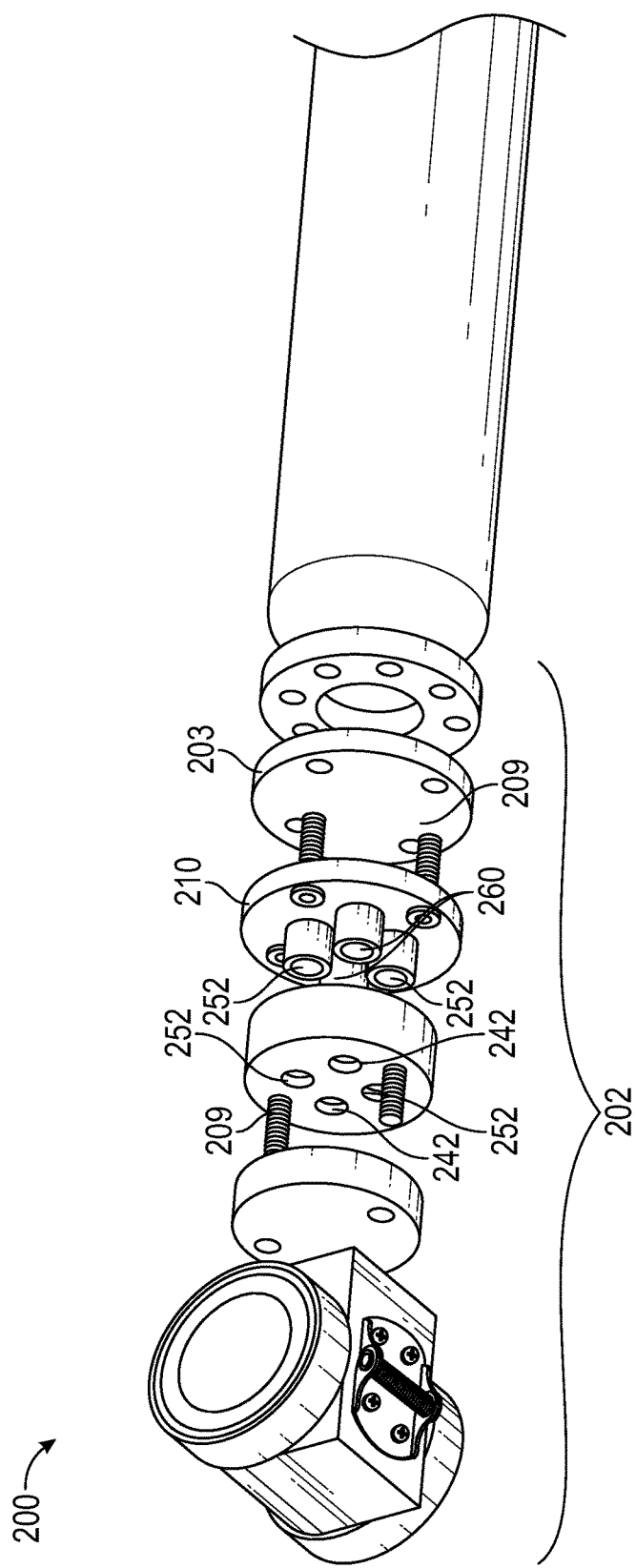
FIG. 18 is a second exploded perspective view of the coupling system of FIG. 15.

In some embodiments, the coupling system 200 can include one or more biasing members 209, as illustrated in FIGS. 17 and 18. The biasing members 209 can be configured and positioned to aid in proper alignment and positioning of the magnetic bodies 252 (magnetic bodies 252 not shown in FIG. 17) within the coupling apparatus 202. In particular, at least a portion of the biasing members 209 can be configured as springs or other structures or apparatuses that are capable of exerting a force on the magnetic bodies 252 to aid in alignment of the magnetic bodies 252. By way of example only, some or all of the biasing members 209 can be configured as compliant metal springs of a length and diameter that is slightly less than some portions of the coupling apparatus 202 (e.g., the plurality of receptacles 240, the plurality of channels 244, and/or the plurality of pegs 254). As such, the biasing members 209 can be used to aid in accurate alignment and positioning of the magnetic bodies 252, as described below.

In some embodiments, at least one biasing member 209 can be used in conjunction within some or all of the plurality of receptacles 240, the plurality of channels 244, and/or the plurality of pegs 254 that include at least one magnetic body 252. For example, as best illustrated in FIG. 17, the magnetic bodies 252 can be placed in the first and third receptacles 240a, 240c and the first and third channels 244a, 244c in the proximal and medial members 206, 208 (i.e., a parallel configuration). In order to secure and align the magnetic bodies 252 within the first and third receptacles 240a, 240c and the first and third channels 244a, 244c, a first biasing member 209a can be positioned (e.g., coupled to the proximal member 208 or uncoupled to the proximal member 208) proximal of the one or more magnetic bodies 252 in the first receptacle 240a and a second biasing member 209b can be positioned proximal of the one or more magnetic bodies 252 in the third receptacle 240c. As a result of this configuration, the biasing members 209a, 209b can bias the magnetic bodies against the flanges 246 (flanges 246 are illustrated in FIG. 18) in the first and third channels 244a, 244c. In other words, when the magnetic bodies 252 are positioned within the first and third receptacles 240a, 240c and the first and third channels 244a, 244c and the medial and proximal members 206, 208 are coupled to the brace member 204, the biasing members 209a, 209b are in a compressed configuration and exert an outward force on the magnetic bodies 252, thereby retaining the magnetic bodies 252 in position during use.

Similarly, the magnetic bodies 252 can be placed in the first and third pegs 254a, 254c in the distal coupling member 210 (i.e., a parallel configuration). In order to secure and align the magnetic bodies 252 within the first and third pegs 254a, 254c, a third biasing member 209c can be positioned distal of the one or more magnetic bodies 252 in the first peg 254a and a fourth biasing member 209d can be positioned distal of the one or more magnetic bodies 252 in the third peg 254c. In particular, the biasing members 209c, 209d can be positioned to engage the proximal face 205 of the backing plate 203, which functions as a backing surface that exerts force on the biasing members 209c, 209d when the distal coupling member 210 is coupled to the robotic arm 201 via the backing plate 203 and the connector plate 262. As a result of this configuration, the biasing members 209c, 209d can bias the magnetic bodies 252 against the peg flanges 260 (peg flanges 260 are illustrated in FIG. 18) in the first and third pegs 254a, 254c. In other words, when the magnetic bodies 252 are positioned within the first and third pegs 254a, 254c and the distal coupling member 210, the backing plate 203, and the connector plate 262 are coupled to the robotic arm 201, the biasing members 209c, 209d are in a compressed configuration and exert an outward force on the magnetic bodies 252, thereby retaining the magnetic bodies 252 in position during use.

EXAMPLES

In order to confirm the functionalities associated with some aspects of the coupling system 100, 200 experiments were conducted to assess the magnetic coupling functionality. In order to perform these experiments, the coupling system 100 was used in conjunction with a robotic arm 101 (i.e., a 7 Degrees of Freedom anthropomorphic robot arm from KUKA Inc.) and an immobile support. In particular, the brace member 104 was affixed to the immobile support in a manner substantially similar to the method described above with respect to positioning a human arm or other appendage within the brace member 104. Thereafter, the robotic arm 101 was removably coupled to the brace member 104 in a manner substantially similar the methods described above.

During each of the following experiments, the robotic arm 101 and the brace member 104 begin in a fully coupled configuration (i.e., with the distal coupling member 110 engaged to the proximal and medial coupling members 106 and 108). Thereafter, the robotic arm 101 pulls away from the brace member 104 in a direction normal to the coupling interface with increasing force until decoupling occurs (i.e., exceeding the attractive force of the mated magnetic bodies 152). The force exerted by the robotic arm 101 starts at 0 N and was increased by 0.125 N/ms until decoupling occurred or until 250 N was reached and the testing was aborted. The robotic arm 101 was controlled in Cartesian impedance mode, so that it developed the force progressively and stoped relatively smoothly after the decoupling event. Eight trials were done for each of the following configurations.

In order to test the adaptive characteristics of the coupling system 100, in terms of the required disengagement force, six different configurations of magnetic bodies 152 were used, as shown in FIG. 12 and in Table 1 below. Each configuration of magnetic bodies 152 had a different theoretical maximum force (i.e., the force needed to decouple the magnetic bodies 152). The configurations tested included different numbers of magnetic bodies 152 put in a parallel configuration (as defined above) or a series configuration (i.e., linearly adjacent or stacked). In particular, the theoretical magnetic body 152-to-magnetic body 152 pull forces of the magnetic bodies 152 used were computed using the information provided by the manufacturing company (K&J Magnetics). In these experiments, two types of magnetic bodies 152 were employed in the six configurations, (i) ⅜ inch diameter step-out magnetic bodies 152a (SD64-OUT, K&J Magnetics) were used exclusively for the point of engagement with the flanges 146 and/or the peg flanges 160 for a contributing force of about 34.7 N each; and (ii) ⅜ inch diameter straight magnetic bodies 152 (D62-N52, K&J Magnetics) were used exclusively stacked behind the step-out magnetic bodies 152a (i.e., in a series configuration) for a contributing force of 2.2N each. Table 1 shows the configurations, amounts of each type of magnetic bodies 152a, 152 used, and total theoretical decoupling force. Finally, for the duration of each trial, the effector force of the robotic arm 101 was measured and recorded at a sampling rate of 500 Hz.

TABLE 1

Experimental Configurations

| Configuration # | # of Step-Out Magnetic Bodies 152a | # of Straight Magnetic Bodies 152 | Theoretical Decoupling Force (N) |
| --- | --- | --- | --- |
| 1 | 1 | 0 | 34.7 |
| 2 | 2 | 0 | 69.4 |
| 3 | 3 | 0 | 104.1 |
| 4 | 4 | 0 | 138.8 |
| 5 | 4 | 2 | 143.2 |
| 6 | 4 | 4 | 147.6 |

Figure 13:
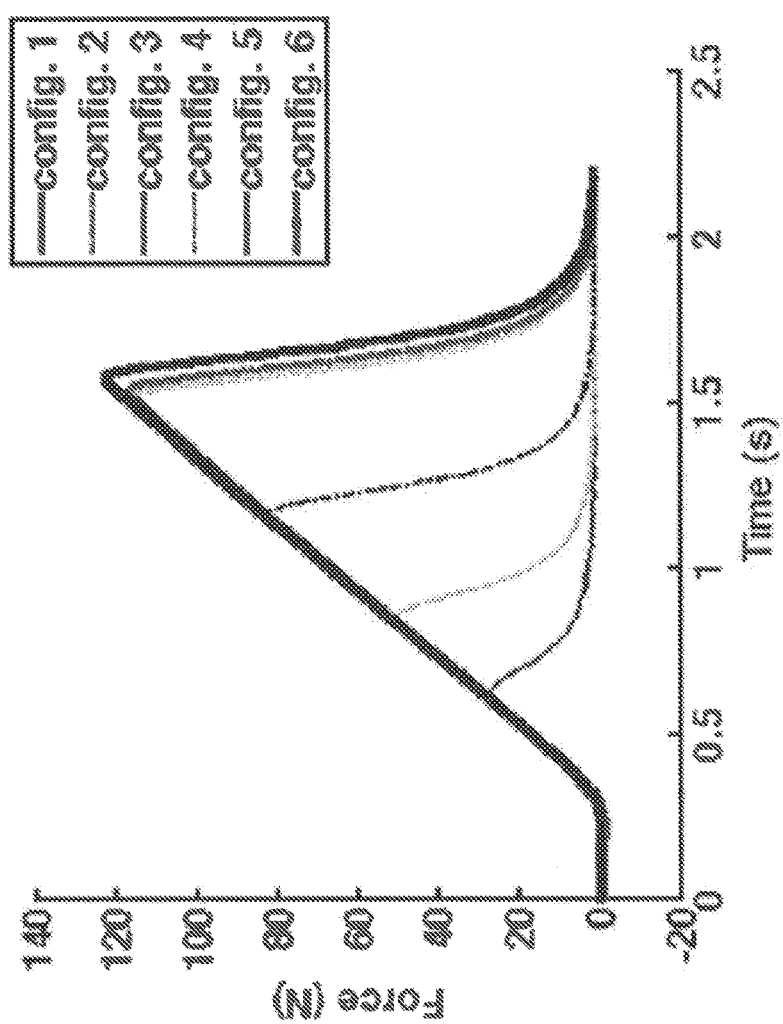
FIG. 13 is a line graph depicting the relationship of force applied by a robotic arm for decoupling using the six different experimental configurations from FIG. 12.
Figure 14:
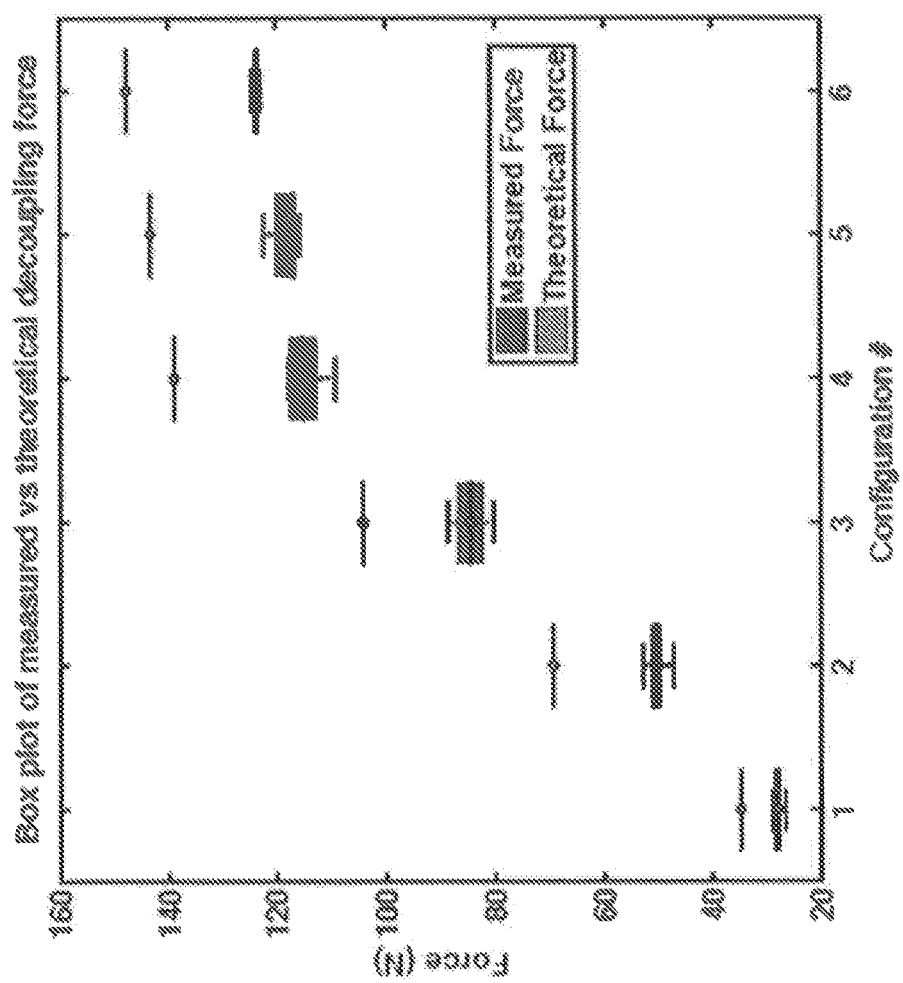
FIG. 14 is a box plot of measured versus theoretical decoupling force across the six different experimental configurations of FIG. 12 using eight trials per configuration.

The recorded force for each trial consistently followed the designed and expected pattern. In particular, the force rose as the robot exerted force, until exceeding the attractive magnetic force and decoupling, at which point measured magnetic force rapidly returned to zero. Moreover, each successive configuration with consecutively greater theoretical force (i.e., stemming from the numbers of magnetic bodies 152a, 152 or the configuration thereof) showed a greater maximum force exerted by the robotic arm 101 just before decoupling occurred. The maximum force of each trial was found and recorded and then grouped by configuration (FIG. 13). Furthermore, a box plot of these maximum forces showing all configurations, means, and standard deviations of maximum force, as compared to the theoretical force for each configuration can be seen in FIG. 14. In addition, Table 2 lists the data found in FIG. 14 in chart form, as well as the mean of the recorded force for each configuration as a percentage of the theoretical (expected) decoupling force for that particular configuration.

The above-described results verify that the coupling system 100 works as expected. In particular, the coupling was consistent for the given configurations and the measured force needed to decouple varied little between trials. Moreover, not only is the coupling system 100 consistent within a single set of parameters (i.e., configuration of the magnetic bodies 152a, 152), it also scales properly as a function of its intended independent variable (i.e., the theoretical decoupling force) achieved via the magnetic bodies 152a, 152. As can be seen by the percentage of the theoretical decoupling force in Table 2, the measured force needed to decouple the coupling system 100 is linearly related and correlates well with the expected decoupling force. For example, the measure force is generally consistently around 80% of the theoretical decoupling force.

TABLE 2

Experimental v. Theoretical Values of Decoupling Force

| Configuration # | Theoretical Decoupling Force (N) | Measured Decoupling Force (N) [Mean ± STD] | Accuracy (%) |
|---|---|---|---|
| 1 | 34.7 | 28.0 ± 0.8 | 80.6 |
| 2 | 69.4 | 50.3 ± 1.7 | 72.5 |
| 3 | 104.1 | 84.5 ± 3.0 | 81.2 |
| 4 | 138.8 | 114.6 ± 3.0 | 82.6 |
| 5 | 143.2 | 118.1 ± 2.4 | 82.4 |
| 6 | 147.6 | 123.5 ± 0.6 | 83.7 |

Figure 21:
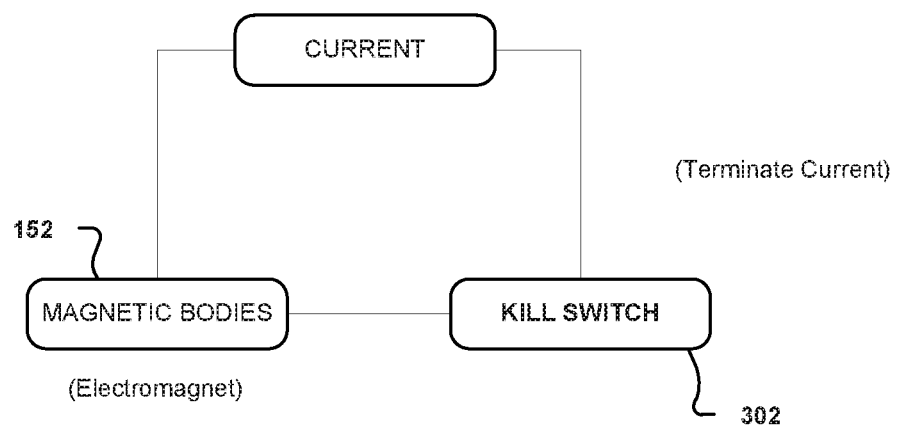
FIG. 21 is a system depicting a kill switch for use with aspects of the present disclosure.
Figure 22:
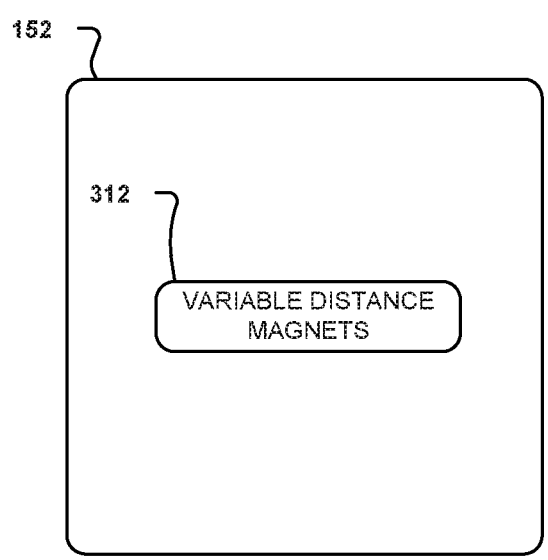
FIG. 22 is a diagram depicting use of variable distance magnets for use with aspects of the present disclosure.
Figure 23:
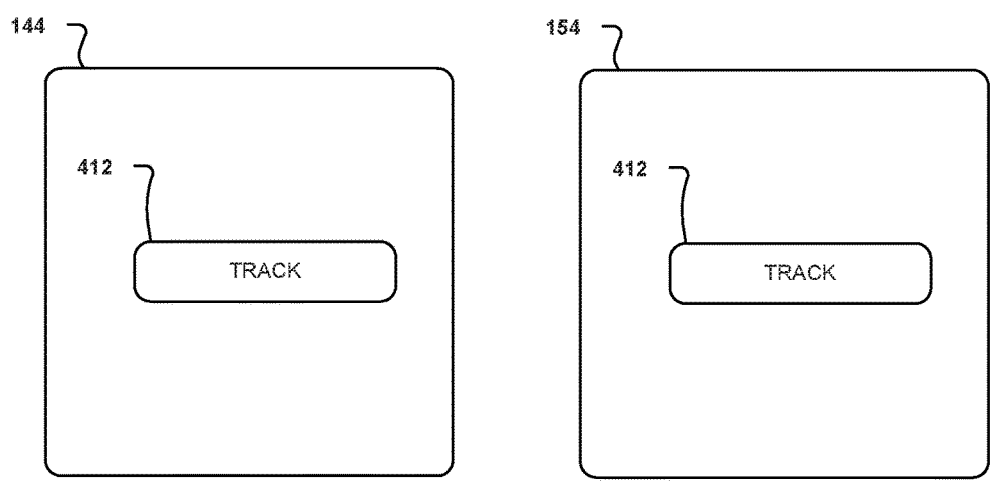
FIG. 23 is a diagram illustrating use of a track according to aspects of the present disclosure.

FIGS. 21-23 illustrate additional possible features for use with the systems and methods of the present disclosure described herein. FIG. 21 shows an implementation of a kill switch 302, for terminating the current supplied to each electromagnet (defined by magnetic bodies 152) according to some embodiments of the present disclosure. FIG. 22 illustrates variable distance magnets 312 which may be engaged to each of a plurality of magnetic bodies 152 according to some embodiments. FIG. 23 illustrates that in other embodiments the plurality of channels 144 and/or the plurality of pegs 154 can include a track 412 as described herein.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A coupling system comprising:
a brace member configured to receive a portion of a human, the brace member including a first portion pivotally coupled to a second portion to collectively define a sleeve channel;
a plurality of coupling members oriented adjacent the brace member, with a first coupling member of the plurality of coupling members being engaged to the brace member, wherein the plurality of coupling members defines a plurality of pegs and defines a plurality of corresponding channels configured to receive a respective one of the plurality of pegs;
a robotic limb engaged to a second coupling member of the plurality of coupling members; and
a plurality of magnetic bodies, wherein at least one of the plurality of magnetic bodies is disposed within any two of the plurality of pegs and at least another one of the plurality of magnetic bodies is disposed with any two of the plurality of corresponding channels,
wherein the sleeve channel is oriented in perpendicular relation relative to the plurality of coupling members,
wherein the plurality of magnetic bodies includes an amount and configuration of magnetic bodies defining a known magnetic decoupling force, and
wherein the second coupling member disengages from the plurality of coupling members and the brace member upon exertion of a predetermined force being applied to the robotic limb so as to disengage the human from the robotic limb, the predetermined force correlating to the known magnetic decoupling force.

2. The coupling system of claim 1, wherein at least one of the plurality of magnetic bodies is disposed within two of the plurality of pegs that are arranged in a parallel configuration.

3. The coupling system of claim 2, wherein at least one of the plurality of magnetic bodies is disposed within two of the plurality of corresponding channels that are arranged in a parallel configuration.

4. The coupling system of claim 1, wherein the brace member comprises at least one strap.

5. The coupling system of claim 1 and further comprising a comfort member.

6. The coupling system of claim 5, wherein the comfort member is disposed at least partially within the sleeve channel.

7. The coupling system of claim 1, further comprising a backing plate coupled to at least one of the plurality of coupling members and a plurality of biasing members.

8. The coupling system of claim 1, further comprising a connector plate disposed between one of the plurality of coupling members and the robotic limb.

9. The coupling system of claim 1, wherein each of the plurality of magnetic bodies is an electromagnet for generating a magnetic field.

10. The coupling system of claim 9, wherein the magnetic field of each electromagnet is controlled by varying a current supplied to each electromagnet.

11. The coupling system of claim 10, wherein each electromagnet is in operative communication with a kill switch for terminating the current supplied to each electromagnet, and wherein the magnetic field for each electromagnet is terminated when the current supplied to each electromagnet is terminated.

12. The coupling system of claim 1, further comprising:
a variable distance apparatus engaged to each of a first plurality of magnetic bodies of the plurality of magnetic bodies for moving the first plurality of magnetic bodies relative to a second plurality of magnetic bodies.

13. The coupling system of claim 12, wherein increasing the distance between the first plurality of magnetic bodies relative to the second plurality of magnetic bodies causes an increase in an attractive magnetic force between the first and second plurality of magnetic bodies.

14. The coupling system of claim 12, wherein decreasing the distance between the first plurality of magnetic bodies relative to the second plurality of magnetic bodies causes a decrease in an attractive magnetic force between the first and second plurality of magnetic bodies.

15. The coupling system of claim 12, wherein the variable distance apparatus comprises a track positioned adjacent the plurality of magnetic bodies for moving a first plurality of magnetic bodies in a linear direction relative to a second plurality of magnetic bodies.

16. A coupling apparatus comprising:
a brace member including a first portion pivotally coupled to a second portion to collectively define a sleeve channel, the brace member configured to engage with a portion of a human;
a proximal coupling member being at least partially engaged to the brace member;
a medial coupling member being at least partially engaged to the proximal coupling member and comprising a plurality of channels;
a distal coupling member defining a plurality of pegs, wherein plurality of channels are configured and arranged to at least partially receive the plurality of pegs, the distal coupling member configured to engage a robotic limb; and a plurality of magnetic bodies, wherein at least one of the plurality of magnetic bodies is disposed within any two of the plurality of pegs and at least another one of the plurality of magnetic bodies is disposed with any two of the plurality of channels;

wherein the distal coupling member is disengageable from the medial coupling member upon exertion of a predetermined force applied to the robotic limb, the predetermined force correlating to a known magnetic decoupling force associated with the plurality of magnetic bodies;

wherein the exertion of the predetermined force being applied to the robot limb is oriented in a direction perpendicular to the sleeve channel.

17. The coupling apparatus of claim 16, wherein at least a portion of the plurality of magnetic bodies comprises a step-out configuration.

18. The coupling apparatus of claim 16, wherein at least one of the plurality of magnetic bodies is disposed within two of the plurality of pegs that are arranged in a parallel configuration.

19. The coupling apparatus of claim 18, wherein at least one of the plurality of magnetic bodies is disposed within two of the plurality of channels that are arranged in a parallel configuration.

20. The coupling apparatus of claim 16, further comprising a backing plate coupled to at least one of the coupling members and a plurality of biasing members.

21. The coupling apparatus of claim 16, further comprising a comfort member.

22. The coupling apparatus of claim 16, wherein at least a portion of the plurality of channels define a flange.

23. The coupling apparatus of claim 22, wherein at least a portion of the plurality of pegs define a peg flange.

24. The coupling apparatus of claim 16, wherein the first portion and the second portion of the brace member are pivotally coupled together using a hinge component.

25. A method of assembling a coupling system, the method comprising:

coupling a first portion to a second portion to form a brace member, wherein the brace member defines a sleeve channel;

coupling a proximal coupling member to the brace member;

coupling a medial coupling member to the proximal coupling member, wherein the medial coupling member comprises a plurality of channels;

coupling a distal coupling member to a robotic limb, wherein the distal coupling member comprises a plurality of pegs, and further wherein the plurality of channels are configured and arranged to receive the plurality of pegs;

disposing at least one of a plurality of magnetic bodies within any two of the plurality of pegs; and disposing at least one of the plurality of magnetic bodies within any two the plurality of channels, wherein the sleeve channel is oriented in perpendicular relation relative to the proximal coupling member.

26. The method of claim 25, wherein at least a portion of the plurality of magnetic bodies comprise a step-out configuration.

27. The method of claim 25, wherein at least one of the plurality of magnetic bodies is disposed within two of the plurality of pegs that are arranged in a parallel configuration and at least one of the plurality of magnetic bodies is disposed within two of the plurality of channels that are arranged in a parallel configuration.

28. The coupling system of claim 1, wherein the exertion of a predetermined force being applied to the robotic limb is made in a direction parallel to the plurality of corresponding channels.

29. The coupling apparatus of claim 16, wherein the proximal coupling member is oriented in perpendicular relation relative to the sleeve channel.

30. The coupling apparatus of claim 16, wherein a single attachment point between the robotic limb and the brace member is defined at a connection between the medial coupling member and the distal coupling member.

* * * * *